US006004535A

United States Patent [19]
Zavada et al.

[11] Patent Number: 6,004,535
[45] Date of Patent: *Dec. 21, 1999

[54] METHODS OF IMAGING NEOPLASTIC DISEASE AND OF DETECTING AND QUANTIFYING MN PROTEIN/POLYPEPTIDE USING MN-SPECIFIC ANTIBODIES

[75] Inventors: Jan Zavada; Silvia Pastorekova; Jaromir Pastorek, all of Bratislava, Czechoslovakia

[73] Assignee: Institute of Virology, Slovak Academy of Sciences, Bratislava, Slovakia

[*] Notice: This patent is subject to a terminal disclaimer.

[21] Appl. No.: 08/335,469

[22] Filed: Nov. 7, 1994

Related U.S. Application Data

[63] Continuation of application No. 07/964,589, Oct. 21, 1992, Pat. No. 5,387,676.

[30] Foreign Application Priority Data

Mar. 11, 1992 [CS] Czechoslovakia ............... 709-92

[51] Int. Cl.⁶ ............... A61K 39/395; A61K 49/00; A61K 51/08; G01N 33/48
[52] U.S. Cl. ............... 424/9.34; 424/9.1; 424/133.1; 424/138.1; 424/141.1; 424/1.49; 435/7.1; 435/7.92; 435/7.23; 435/7.93; 530/387.1; 530/388.1; 530/388.2
[58] Field of Search ............... 424/130.1, 133.1, 424/138.1, 139.1, 141.1, 9.34, 1.49, 9.1, 155.1; 435/7.1, 7.23, 7.92, 7.93; 530/387.1, 388.1, 388.2

[56] References Cited

U.S. PATENT DOCUMENTS 5,387,676  2/1995  Zavada et al. ............... 536/23.5

FOREIGN PATENT DOCUMENTS 9007861  7/1990  Austria.
8808854  11/1988  WIPO.
9534650  12/1995  WIPO.

OTHER PUBLICATIONS

Uemura et al., "Expression of Tumor–Associated Antigen MN/G250 in Urologic Carcinoma: Potential Therapeutic Target," *J. Urology:* 157 (4 Supp): 377 (Abstract 1475) (Apr. 16, 1997).
Svoboda, J., "Malignant Interaction of Rous Virus With Mammalian Cells In Vivo and In Vitro, "*National Cancer Institute Monograph No. 17, N:* "International Conference on Avian Tumor Virus "(J. W. Beard ed.) , pp. 277–298 (1964).
Ballou et al., "Tumor location detected with radioactively labeled monoclonal antibody and external scintigraphy, "*Science*, 206: 844–846 (1979).
Chan and Sikora, "The potential of oncogene products as tumour markers," *Cancer Surveys*, 6(2): 185–207 (1987).

Epenetos et al., "Radioimmunodiagnosis of Ovarian Cancer Using $^{123}$I–Labelled, Tumor–Associated Monoclonal Antibodies, "*Cancer Detection and Prevention*, 7: 45–49 (1984).
Gitsch et al., "Diagnostic and intraoperative immunoscintigraphy in ovarian cancer," *European Journal of Obstetrics & Gynecology and Reproductive Biology*, 32: 33–45 (1989).
Jabaari et al., "Elevated expression of the interleukin 4 receptor in carcinoma: a target for immunotherapy?, "*Br. J. Cancer*, 59: 910–914 (1989).
Katoh et al., "Immunoscintigraphy of Human Tumors Transplanted in Nude Mice with Radiolabeled Anti–ras p21 Monoclonal Antibodies, "*The Journal of Nuclear Medicine*, 31(9): 1520–1526 (Sep. 1990).
Kenemans et al., "Clinical applications of monoclonal antibodies against ovarian cancer–associated antigens, "*European Journal of Obstetrics & Gynecology and Reproductive Biology*, 29: 207–218 (1988).
Park et al., "Anti–p185HER2 monoclonal antibodies: Biological properties and potential for immunotherapy,"Chapter 10 of *Genes, Oncogenes and Hormones: Advances in Cellular and Molecular Biology of Breast Cancer*[Eds. Dickson and Lippman; Kluwer Academic Press; Boston, MA, USA (1991)].
Divgi et al., "Scintigraphy of Renal Cell Carcinoma with I–131 Labelled Monoclonal Antobody (MAB G250, "*European Journal of Nuclear Medicine*, 19(8): 578 (Abstract) Aug. 23, 1992).
Kurth et al., "Characterization of Human Renal Cell Carcinoma Tumor Lines by Means of Monoclonal Antibodies, "*Prostate*, 6(4): 451 (Abstract) (1985).
Oosterwijk et al., "The Expression of Renal Antigens in Renal Cell Carcinoma, "*World Journal of Urology*, 2(2): 156–158 (1984).
Oosterwijk et al., "Monclonal Antibodies that Discriminate Between Renal Cell Carcinomas (RCC) and other Malignancies,"*Prostate*, 6(4): 451–452 (1985).
Oosterwijk et al., "Immunohistochemical Analysis of Monoclonal Antibodies to Renal Antigens —Application in the Diagnosis of Renal Cell Carcinoma, "*American Journal of Pathology*, 123(2): 301–309 (May 1986).
Oosterwijk et al., "Monoclonal Antibody G250 Recognizes a Determinant Present in Renal–Cell Carcinoma and Absent from Normal Kidney, "*Int. J. Cancer*, 38: 489–494 (1986).

(List continued on next page.)

*Primary Examiner*—Julie Burke
*Attorney, Agent, or Firm*—Leona L. Lauder; Arthur S. Morgenstern

[57] ABSTRACT

A new gene—MN—and proteins/polypeptides encoded therefrom are disclosed. Recombinant nucleic acid molecules for expressing MN proteins/polypeptides and fusion proteins are provided. Expression of the MN gene is disclosed as being associated with tumorigenicity, and the invention concerns methods and compositions for detecting and/or quantitating MN antigen and/or MN-specific antibodies in vertebrate samples that are diagnostic/prognostic for neoplastic and pre-neoplastic disease. MN-specific antibodies are disclosed that can be used diagnostically/prognostically, therapeutically, for imaging, and for affinity purification of MN proteins/polypeptides.

23 Claims, 10 Drawing Sheets

OTHER PUBLICATIONS

Oosterwijk et al., "Relationship Between DNA Ploidy, Antigen Expression and Survival in Renal Cell Carcinoma, "*Int. J. Cancer*, 42: 703–708 (1988).

Oosterwijk et al., "Expression of Intermediater–sized Filaments in Developing and Adult Human Kidney and Renal Cell Carcinoma, "*The Journal of Histochemistry and Cytochemistry*, 38(3): 385–392 (1990).

Oosterwijk et al., "Molecular characterization of the Renal Cell Carcinoma–associated antigen G250, "*Proceedings of the American Association for Cancer Research*, 37: 461 (Mar. 1996).

Frohman et al., "Rapid production of full–length cDNAs from rare transcripts: Amplification using a single gene–specific oligonucleotide primer, "*PNAS(USA)*, 85: 8998–9002 (Dec. 1988).

Frosch et al., "Cloning and Characterisation of an immunodominant Major Surface Antigen of *Echinococcus multilocularis*", *Molecular and Biochemical Parasitology*, 48: 121–130 (1991).

Pastorekova et al., "A Novel Quasi–viral Agent, MaTU, is a Two–Component System, "*Virology*, 187: 620–626 (1992).1

Stanbridge et al., "Specific Chromosome Loss Associated with the Expression of Tumorigenicity in Human Cell Hybrids ", *Somatic Cell Genetics*, 7(6): 699–712 (1981).

Stanbridge et al., "Human Cell Hybrids: Analysis of Transformation and Tumorigenicity ", *Science*, 215: 252–259 (Jan. 15, 1982).

Tweedle and Edwards, "Mouse Carbonic Anhydrase III: Nucleotide Sequence and Expression Studies ", *Biochemical Genetics*, 27(1/2):17–30 (1989).

Young and Davis, "Efficient Isolation of Genes by Using Antibody Probes ", *PNAS*(USA) 80: 1194–1198 (Mar. 1983).

Zavada, "The Pseudotypic Paradox ", *J. gen. Virol.*, 63: 15–24 (1982).

Zavada and Zavadova, "A Transmissible Antigen Detected in Two Cell Lines Derived from Human Tumours ", *J. gen. Virol.*, 24: 327–337 (1974).

Zavada and Zavadova, "An unusual transmissible agent —MaTu ", *Arch. Virol.*, 118: 189–197 (1991).

Zavada et al., "VSV Pseudotype Produced in Cell Line derived from Human Mammary Carcinoma ", *Nature New Biology*, 240: 124–125 (Nov. 22, 1972).

Zavada et al., "Tumorigenicity–Related Expression of MaTu Proteins in HeLa x Fibroblast Hybrids ", Abstract presented at the XIX Meeting of the European Tumor Virus Group (May 1–4, 1991).

Zavada et al Int J Cancer vol. 54 268–274, 1993.

Pastorek et al Oncogene vol. 9 1877–1888, 1994.

Costa Human Pathology, vol. 27, No. 3 217–219, Mar. 1996.

Huston et al (1988) Proc. Nat'l Acad. Ser. 85: 5879–5883.

Eary et al (1989) J. Nucl. Med. 30: 25–32.

Mage (1980) Meth. Enzymol. 70: 142–150.

Zavada et al Arch Virol 118:189–97 (1991).

Pastorekova et al, Virol. 187:620–626 (1992).

Harlow et al, Cold Spe. Harlow, NY, ch 6,9,10,12; pp. 630–631, 184–185, 1988.

| | | | | | | | | | | | | | | | |
|---|---|---|---|---|---|---|---|---|---|---|---|---|---|---|---|
| 1 | Gln | Arg | Leu | Pro | Arg | Met | Gln | Glu | Asp | Ser | Pro | Leu | Gly | Gly | Gly |
| 1 | CAG | AGG | TTG | CCC | CGG | ATG | CAG | GAG | GAT | TCC | CCC | TTG | GGA | GGA | GGC |
| 16 | Ser | Ser | Gly | Glu | Asp | Asp | Pro | Leu | Gly | Glu | Glu | Asp | Leu | Pro | Ser |
| 46 | TCT | TCT | GGG | GAA | GAT | GAC | CCA | CTG | GGC | GAG | GAG | GAT | CTG | CCC | AGT |
| 31 | Glu | Glu | Asp | Ser | Pro | Arg | Glu | Glu | Asp | Pro | Pro | Gly | Glu | Glu | Asp |
| 91 | GAA | GAG | GAT | TCA | CCC | AGA | GAG | GAG | GAT | CCA | CCC | GGA | GAG | GAG | GAT |
| 46 | Leu | Pro | Gly | Glu | Glu | Asp | Leu | Pro | Gly | Glu | Glu | Asp | Leu | Pro | Glu |
| 136 | CTA | CCT | GGA | GAG | GAG | GAT | CTA | CCT | GGA | GAG | GAG | GAT | CTA | CCT | GAA |
| 61 | Val | Lys | Pro | Lys | Ser | Glu | Glu | Glu | Gly | Ser | Leu | Lys | Leu | Glu | Asp |
| 181 | GTT | AAG | CCT | AAA | TCA | GAA | GAA | GAG | GGC | TCC | CTG | AAG | TTA | GAG | GAT |
| 76 | Leu | Pro | Thr | Val | Glu | Ala | Pro | Gly | Asp | Pro | Gln | Glu | Pro | Gln | Asn |
| 226 | CTA | CCT | ACT | GTT | GAG | GCT | CCT | GGA | GAT | CCT | CAA | GAA | CCC | CAG | AAT |
| 91 | Asn | Ala | His | Arg | Asp | Lys | Glu | Gly | Asp | Asp | Gln | Ser | His | Trp | Arg |
| 271 | AAT | GCC | CAC | AGG | GAC | AAA | GAA | GGG | GAT | GAC | CAG | AGT | CAT | TGG | CGC |
| 106 | Tyr | Gly | Gly | Asp | Pro | Pro | Trp | Pro | Arg | Val | Ser | Pro | Ala | Cys | Ala |
| 316 | TAT | GGA | GGC | GAC | CCG | CCC | TGG | CCC | CGG | GTG | TCC | CCA | GCC | TGC | GCG |
| 121 | Gly | Arg | Phe | Gln | Ser | Pro | Val | Asp | Ile | Arg | Pro | Gln | Leu | Ala | Ala |
| 361 | GGC | CGC | TTC | CAG | TCC | CCG | GTG | GAT | ATC | CGC | CCC | CAG | CTC | GCC | GCC |
| 136 | Phe | Cys | Pro | Ala | Leu | Arg | Pro | Leu | Glu | Leu | Leu | Gly | Phe | Gln | Leu |
| 406 | TTC | TGC | CCG | GCC | CTG | CGC | CCC | CTG | GAA | CTC | CTG | GGC | TTC | CAG | CTC |
| 151 | Pro | Pro | Leu | Pro | Glu | Leu | Arg | Leu | Arg | Asn | Asn | Gly | His | Ser | Val |
| 451 | CCG | CCG | CTC | CCA | GAA | CTG | CGC | CTG | CGC | AAC | AAT | GGC | CAC | AGT | GTG |
| 166 | Gln | Leu | Thr | Leu | Pro | Pro | Gly | Leu | Glu | Met | Ala | Leu | Gly | Pro | Gly |
| 496 | CAA | CTG | ACC | CTG | CCT | CCT | GGG | CTA | GAG | ATG | GCT | CTG | GGT | CCC | GGG |
| 191 | Arg | Glu | Tyr | Arg | Ala | Leu | Gln | Leu | His | Leu | His | Trp | Gly | Ala | Ala |
| 541 | CGG | GAG | TAC | CGG | GCT | CTG | CAG | CTG | CAT | CTG | CAC | TGG | GGG | GCT | GCA |
| 196 | Gly | Arg | Pro | Gly | Ser | Glu | His | Thr | Val | Glu | Gly | His | Arg | Phe | Pro |
| 586 | GGT | CGT | CCG | GGC | TCG | GAG | CAC | ACT | GTG | GAA | GGC | CAC | CGT | TTC | CCT |
| 211 | Ala | Glu | Ile | His | Val | Val | His | Leu | Ser | Thr | Ala | Phe | Ala | Arg | Val |
| 631 | GCC | GAG | ATC | CAC | GTG | GTT | CAC | CTC | AGC | ACC | GCC | TTT | GCC | AGA | GTT |

FIG._1A

| | | | | | | | | | | | | | | |
|---|---|---|---|---|---|---|---|---|---|---|---|---|---|---|
| 226 | Asp | Glu | Ala | Leu | Gly | Arg | Pro | Gly | Gly | Leu | Ala | Val | Leu | Ala | Ala |
| 676 | GAC | GAG | GCC | TTG | GGG | CGC | CCG | GGA | GGC | CTG | GCC | GTG | TTG | GCC | GCC |
| 241 | Phe | Leu | Glu | Glu | Gly | Pro | Glu | Glu | Asn | Ser | Ala | Tyr | Glu | Gln | Leu |
| 721 | TTT | CTG | GAG | GAG | GGC | CCG | GAA | GAA | AAC | AGT | GCC | TAT | GAG | CAG | TTG |
| 256 | Leu | Ser | Arg | Leu | Glu | Glu | Ile | Ala | Glu | Glu | Gly | Ser | Glu | Thr | Gln |
| 766 | CTG | TCT | CGC | TTG | GAA | GAA | ATC | GCT | GAG | GAA | GGC | TCA | GAG | ACT | CAG |
| 271 | Val | Pro | Gly | Leu | Asp | Ile | Ser | Ala | Leu | Leu | Pro | Ser | Asp | Phe | Ser |
| 811 | GTC | CCA | GGA | CTG | GAC | ATA | TCT | GCA | CTC | CTG | CCC | TCT | GAC | TTC | AGC |
| 286 | Arg | Tyr | Phe | Gln | Tyr | Glu | Gly | Ser | Leu | Thr | Thr | Pro | Pro | Cys | Ala |
| 856 | CGC | TAC | TTC | CAA | TAT | GAG | GGG | TCT | CTG | ACT | ACA | CCG | CCC | TGT | GCC |
| 301 | Gln | Gly | Val | Ile | Trp | Thr | Val | Phe | Asn | Gln | Thr | Val | Met | Leu | Ser |
| 901 | CAG | GGT | GTC | ATC | TGG | ACT | GTG | TTT | AAC | CAG | ACA | GTG | ATG | CTG | AGT |
| 316 | Ala | Lys | Gln | Leu | His | Thr | Leu | Ser | Asp | Thr | Leu | Trp | Gly | Pro | Gly |
| 946 | GCT | AAG | CAG | CTC | CAC | ACC | CTC | TCT | GAC | ACC | CTG | TGG | GGA | CCT | GGT |
| 331 | Asp | Ser | Arg | Leu | Gln | Leu | Asn | Phe | Arg | Ala | Thr | Gln | Pro | Leu | Asn |
| 991 | GAC | TCT | CGG | CTA | CAG | CTG | AAC | TTC | CGA | GCG | ACG | CAG | CCT | TTG | AAT |
| 346 | Gly | Arg | Val | Ile | Glu | Ala | Ser | Phe | Pro | Ala | Gly | Val | Asp | Ser | Ser |
| 1046 | GGG | CGA | GTG | ATT | GAG | GCC | TCC | TTC | CCT | GCT | GGA | GTG | GAC | AGC | AGT |
| 361 | Pro | Arg | Ala | Ala | Glu | Pro | Val | Gln | Leu | Asn | Ser | Cys | Leu | Ala | Ala |
| 1081 | CCT | CGG | GCT | GCT | GAG | CCA | GTC | CAG | CTG | AAT | TCC | TGC | CTG | GCT | GCT |
| 376 | Gly | Asp | Ile | Leu | Ala | Leu | Val | Phe | Gly | Leu | Leu | Phe | Ala | Val | Thr |
| 1126 | GGT | GAC | ATC | CTA | GCC | CTG | GTT | TTT | GGC | CTC | CTT | TTT | GCT | GTC | ACC |
| 391 | Ser | Val | Ala | Phe | Leu | Val | Gln | Met | Arg | Arg | Gln | His | Arg | Arg | Gly |
| 1171 | AGC | GTC | GCG | TTC | CTT | GTG | CAG | ATG | AGA | AGG | CAG | CAC | AGA | AGG | GGA |
| 406 | Thr | Lys | Gly | Gly | Val | Ser | Tyr | Arg | Pro | Ala | Glu | Val | Ala | Glu | Thr |
| 1216 | ACC | AAA | GGG | GGT | GTG | AGC | TAC | CGC | CCA | GCA | GAG | GTA | GCC | GAG | ACT |
| 421 | Gly | Ala | | | | | | | | | | | | | |
| 1261 | GGA | GCC | TAG | AGG | CTG | GAT | CTT | GGA | GAA | TGT | GAG | AAG | CCA | GCC | AGA |
| 1306 | GGC | ATC | TGA | GGG | GGA | GCC | GGT | AAC | TGT | CCT | GTC | CTG | CTC | ATT | ATG |
| 1351 | CCA | CTT | CCT | TTT | AAC | TGC | CAA | GAA | ATT | TTT | TAA | AAT | AAA | TAT | TTA |
| 1396 | TAA | T | | | | | | | | | | | | | |

FIG._1B

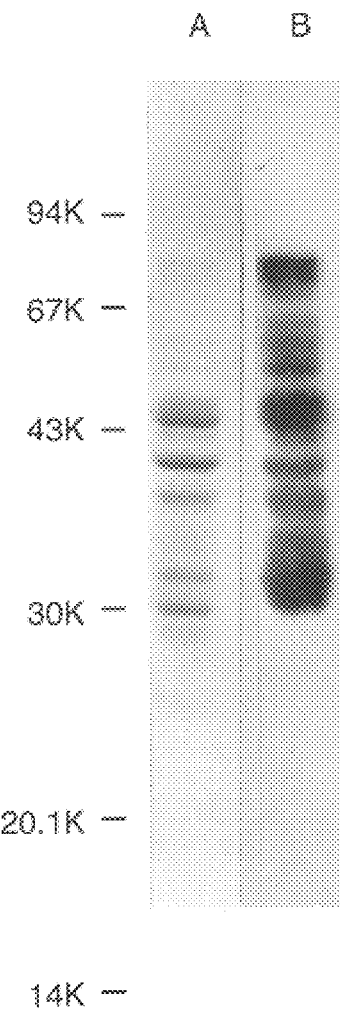
FIG._2
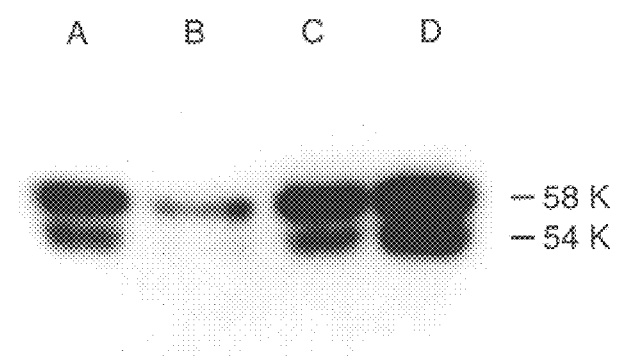
FIG._3

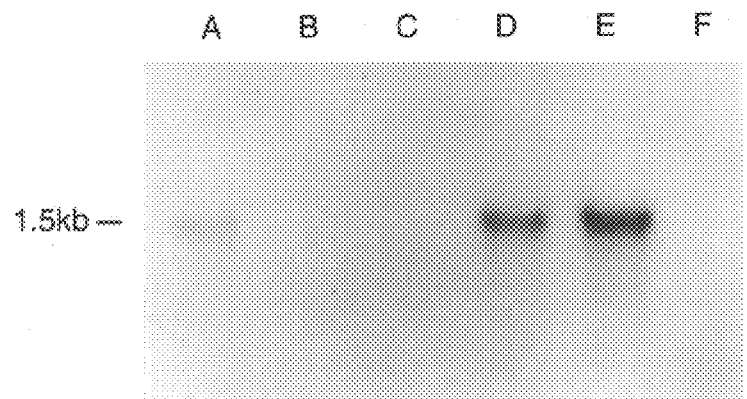
FIG._4
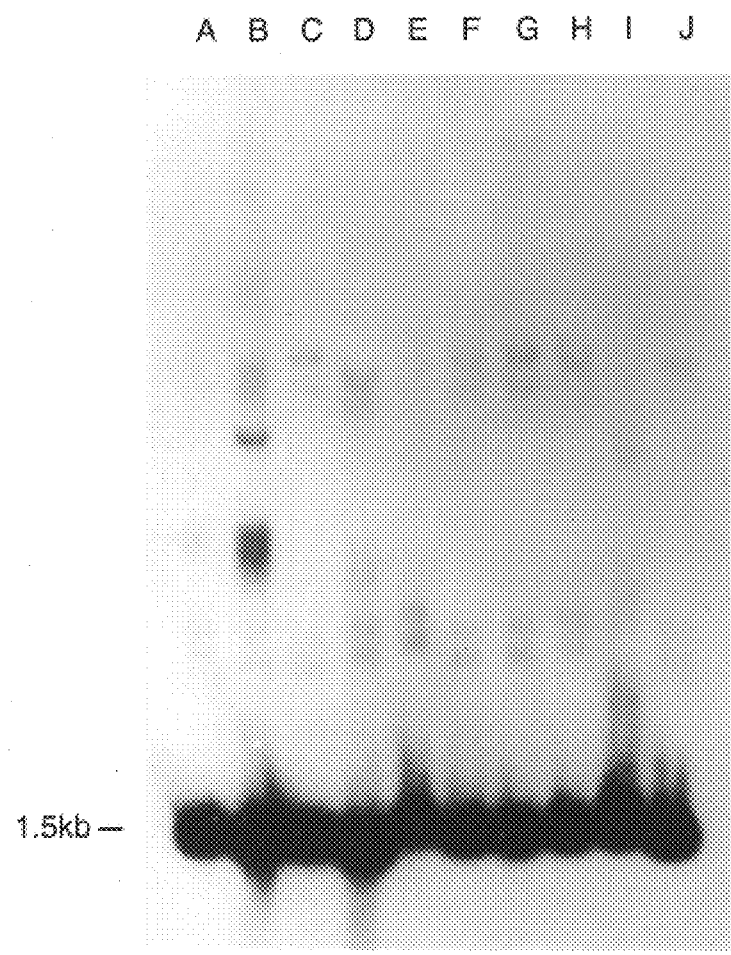
FIG._5

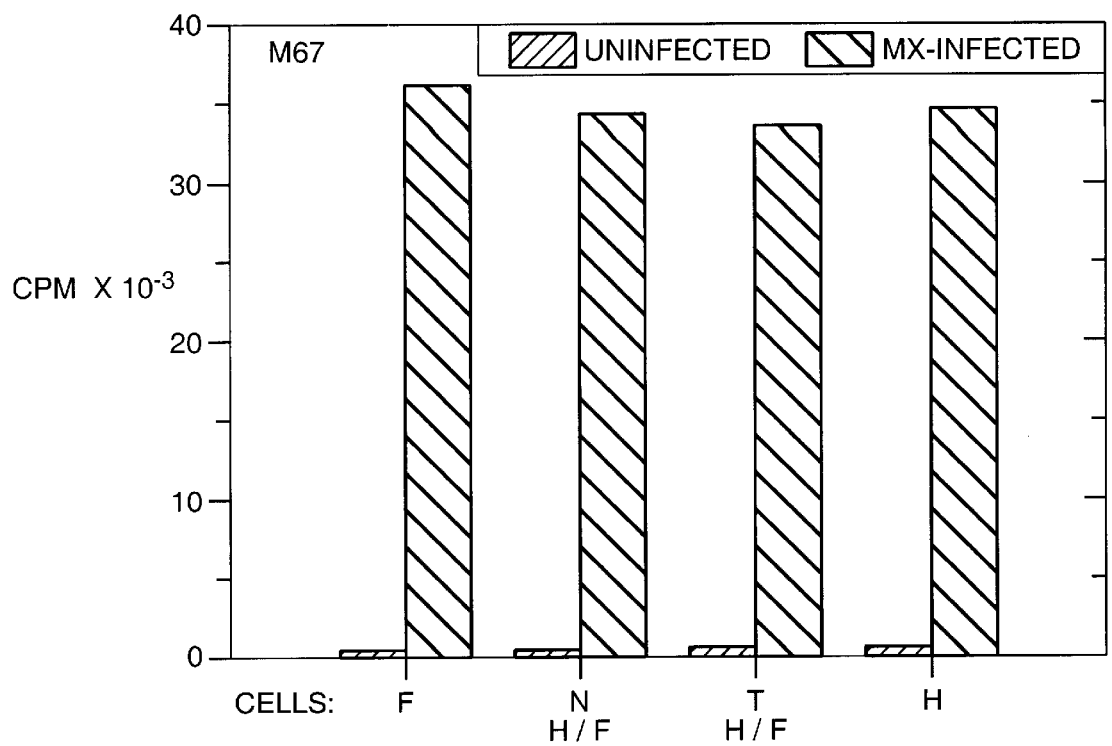
FIG._6A
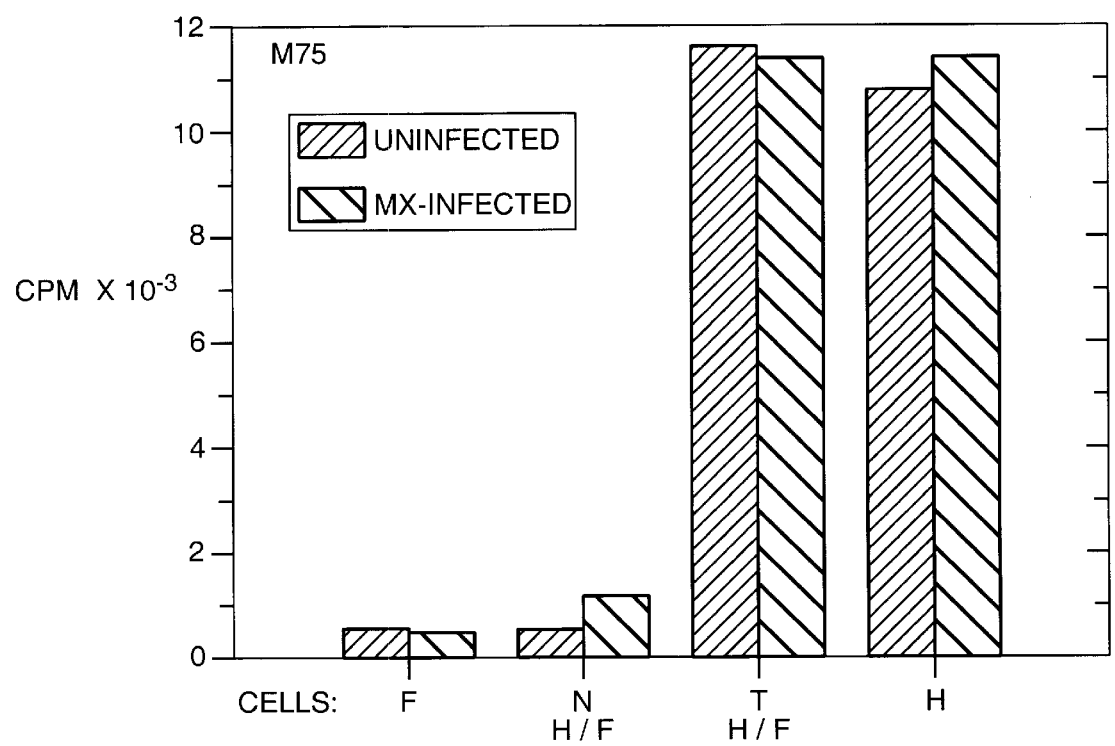
FIG._6B

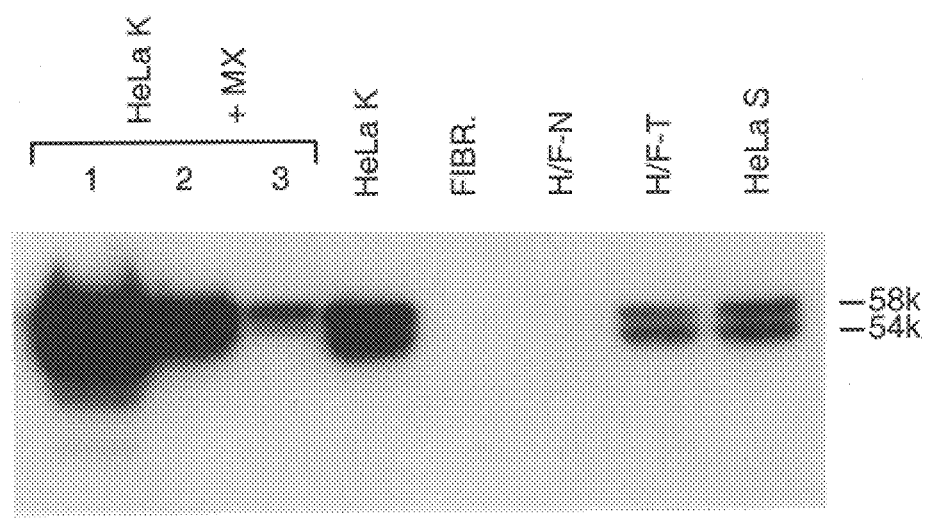
FIG._7
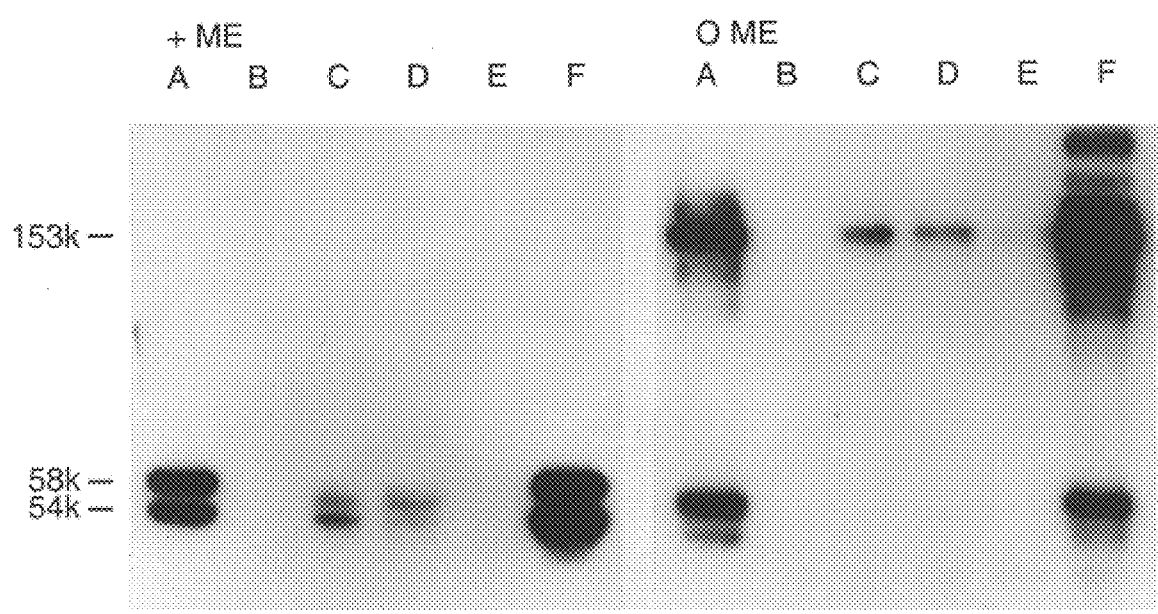
FIG._8

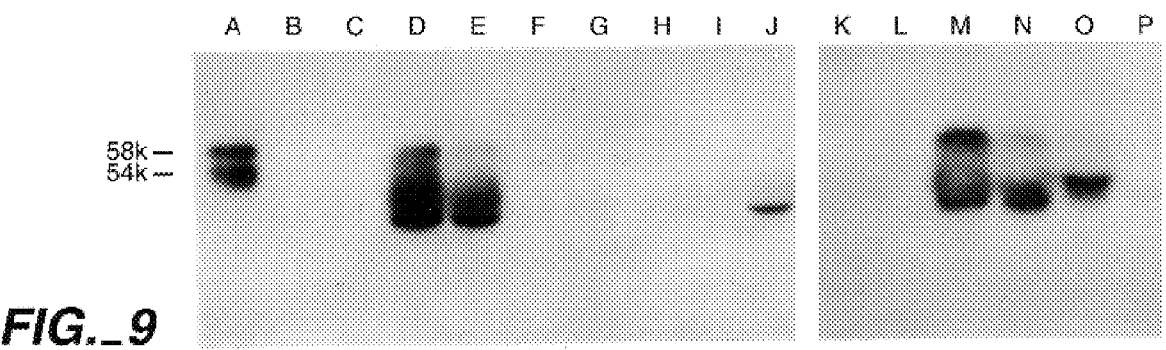
FIG._9
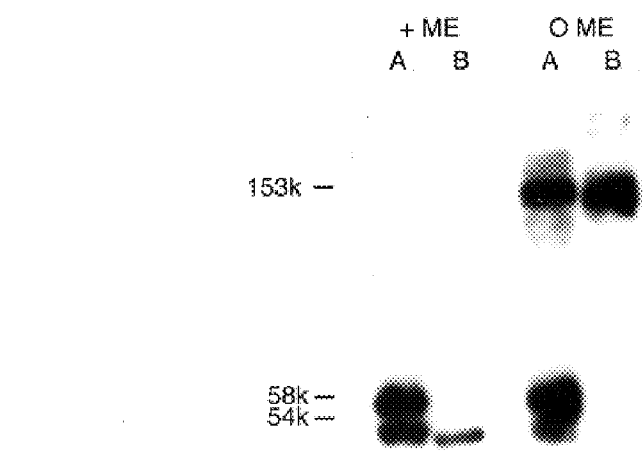
FIG._10

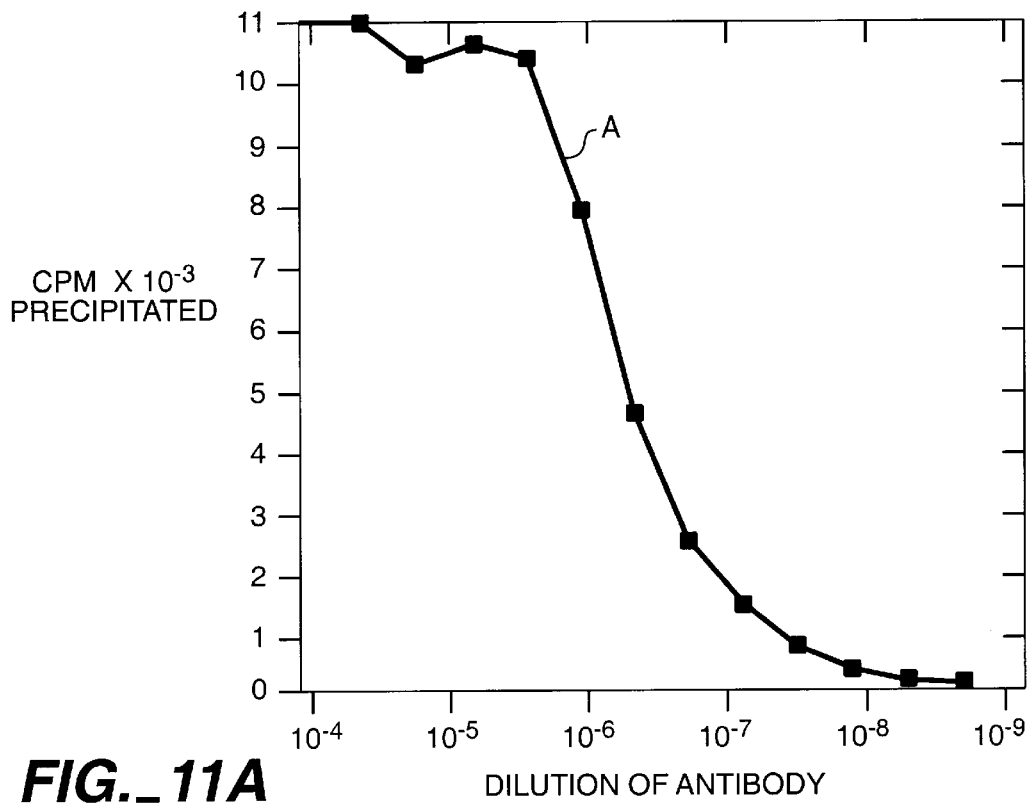
FIG._11A
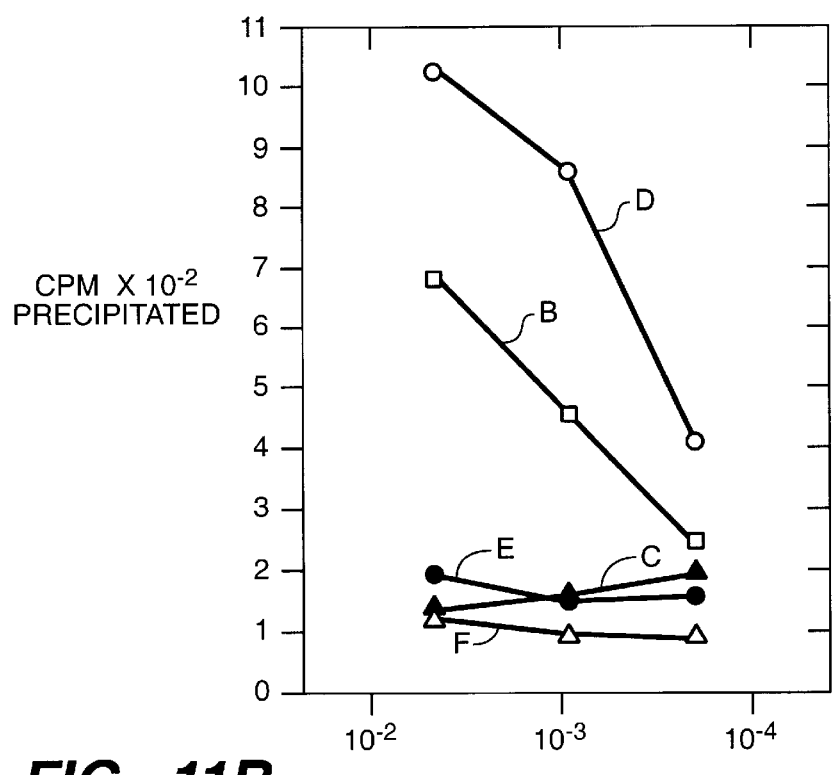
FIG._11B

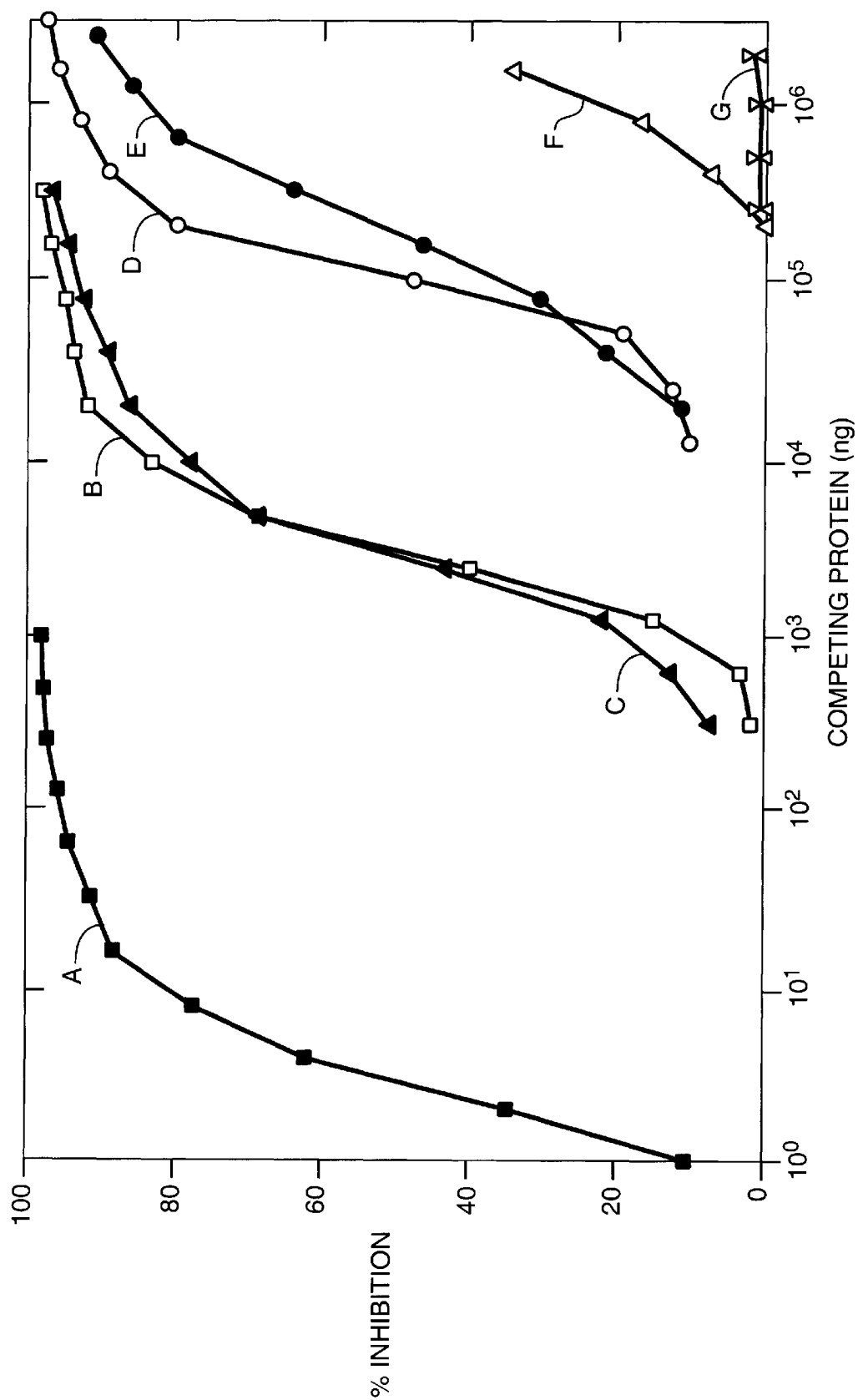
FIG._12

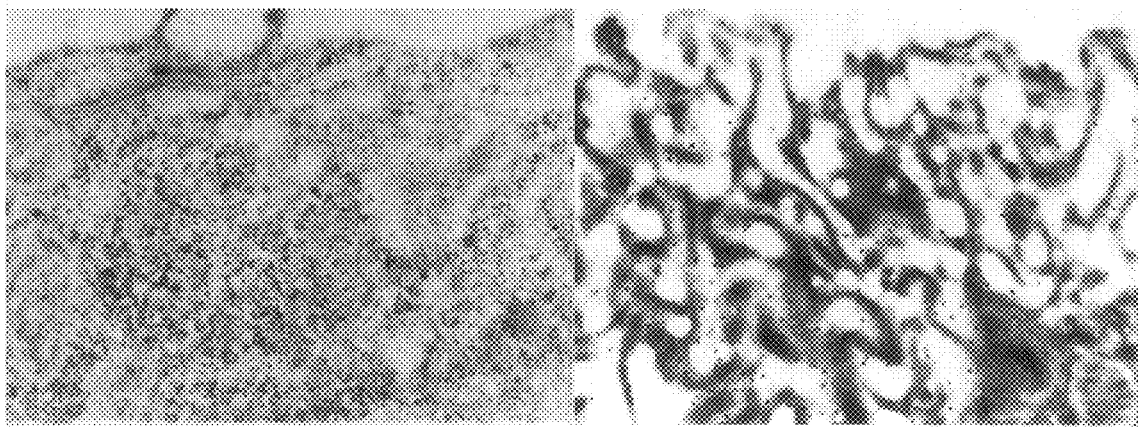
FIG._13A  FIG._13B
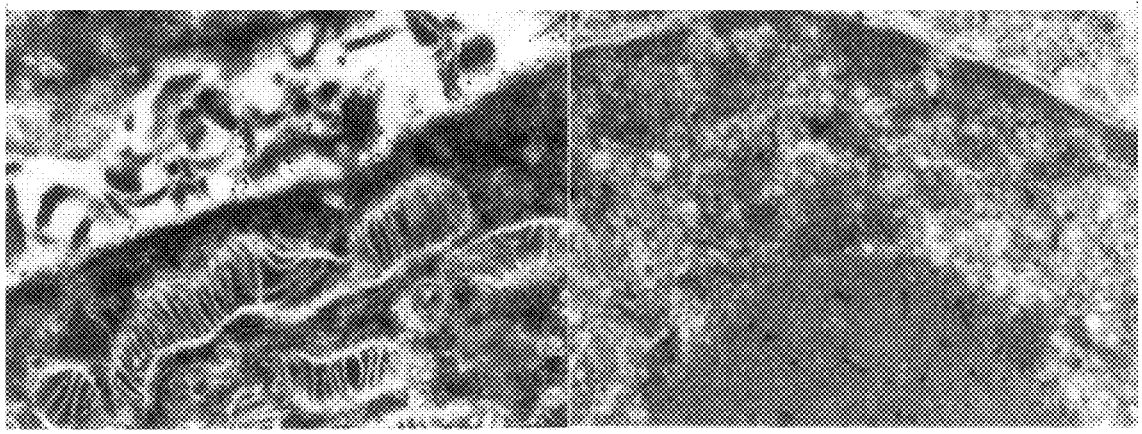
FIG._13C  FIG._13D
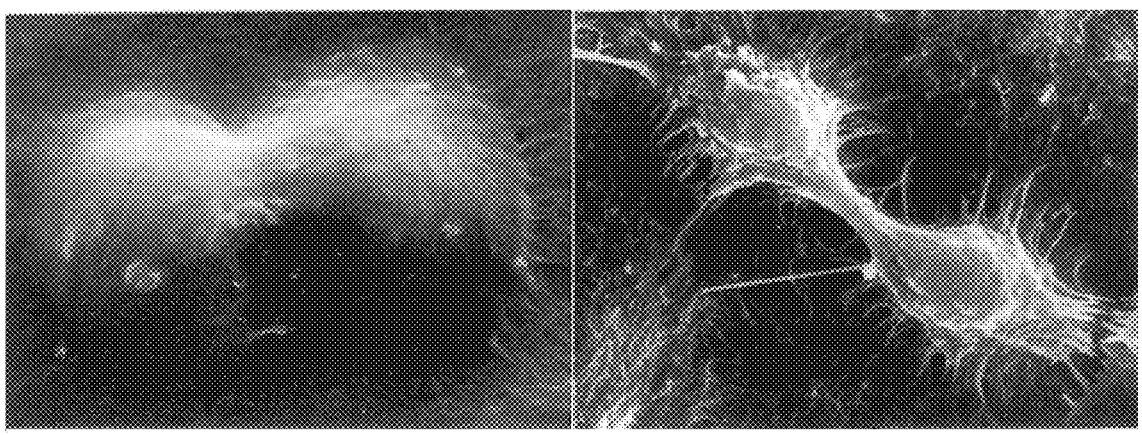
FIG._13E  FIG._13F

SEQUENCE LISTING

<160> NUMBER OF SEQ ID NOS: 4

<210> SEQ ID NO 1
<211> LENGTH: 1399
<212> TYPE: DNA
<213> ORGANISM: Human
<220> FEATURE:
<221> NAME/KEY: CDS
<222> LOCATION: (1)..(1266)

<400> SEQUENCE: 1

```
cag agg ttg ccc cgg atg cag gag gat tcc ccc ttg gga gga ggc tct      48
Gln Arg Leu Pro Arg Met Gln Glu Asp Ser Pro Leu Gly Gly Gly Ser
 1               5                  10                  15 tct ggg gaa gat gac cca ctg ggc gag gag gat ctg ccc agt gaa gag      96
Ser Gly Glu Asp Asp Pro Leu Gly Glu Glu Asp Leu Pro Ser Glu Glu
                20                  25                  30 gat tca ccc aga gag gag gat cca ccc gga gag gag gat cta cct gga     144
Asp Ser Pro Arg Glu Glu Asp Pro Pro Gly Glu Glu Asp Leu Pro Gly
            35                  40                  45 gag gag gat cta cct gga gag gag gat cta cct gaa gtt aag cct aaa     192
Glu Glu Asp Leu Pro Gly Glu Glu Asp Leu Pro Glu Val Lys Pro Lys
        50                  55                  60 tca gaa gaa gag ggc tcc ctg aag tta gag gat cta cct act gtt gag     240
Ser Glu Glu Glu Gly Ser Leu Lys Leu Glu Asp Leu Pro Thr Val Glu
 65                 70                  75                  80 gct cct gga gat cct caa gaa ccc cag aat aat gcc cac agg gac aaa     288
Ala Pro Gly Asp Pro Gln Glu Pro Gln Asn Asn Ala His Arg Asp Lys
                85                  90                  95 gaa ggg gat gac cag agt cat tgg cgc tat gga ggc gac ccg ccc tgg     336
Glu Gly Asp Asp Gln Ser His Trp Arg Tyr Gly Gly Asp Pro Pro Trp
            100                 105                 110 ccc cgg gtg tcc cca gcc tgc gcg ggc cgc ttc cag tcc ccg gtg gat     384
Pro Arg Val Ser Pro Ala Cys Ala Gly Arg Phe Gln Ser Pro Val Asp
        115                 120                 125 atc cgc ccc cag ctc gcc gcc ttc tgc ccg gcc ctg cgc ccc ctg gaa     432
Ile Arg Pro Gln Leu Ala Ala Phe Cys Pro Ala Leu Arg Pro Leu Glu
    130                 135                 140 ctc ctg ggc ttc cag ctc ccg ccg ctc cca gaa ctg cgc ctg cgc aac     480
Leu Leu Gly Phe Gln Leu Pro Pro Leu Pro Glu Leu Arg Leu Arg Asn
145                 150                 155                 160 aat ggc cac agt gtg caa ctg acc ctg cct cct ggg cta gag atg gct     528
Asn Gly His Ser Val Gln Leu Thr Leu Pro Pro Gly Leu Glu Met Ala
                165                 170                 175 ctg ggt ccc ggg cgg gag tac cgg gct ctg cag ctg cat ctg cac tgg     576
Leu Gly Pro Gly Arg Glu Tyr Arg Ala Leu Gln Leu His Leu His Trp
            180                 185                 190 ggg gct gca ggt cgt ccg ggc tcg gag cac act gtg gaa ggc cac cgt     624
Gly Ala Ala Gly Arg Pro Gly Ser Glu His Thr Val Glu Gly His Arg
        195                 200                 205 ttc cct gcc gag atc cac gtg gtt cac ctc agc acc gcc ttt gcc aga     672
Phe Pro Ala Glu Ile His Val Val His Leu Ser Thr Ala Phe Ala Arg
    210                 215                 220 gtt gac gag gcc ttg ggg cgc ccg gga ggc ctg gcc gtg ttg gcc gcc     720
Val Asp Glu Ala Leu Gly Arg Pro Gly Gly Leu Ala Val Leu Ala Ala
225                 230                 235                 240 ttt ctg gag gag ggc ccg gaa gaa aac agt gcc tat gag cag ttg ctg     768
Phe Leu Glu Glu Gly Pro Glu Glu Asn Ser Ala Tyr Glu Gln Leu Leu
                245                 250                 255 tct cgc ttg gaa gaa atc gct gag gaa ggc tca gag act cag gtc cca     816
```

```
        Ser Arg Leu Glu Glu Ile Ala Glu Gly Ser Glu Thr Gln Val Pro
                260                 265                 270 gga ctg gac ata tct gca ctc ctg ccc tct gac ttc agc cgc tac ttc       864
Gly Leu Asp Ile Ser Ala Leu Leu Pro Ser Asp Phe Ser Arg Tyr Phe
            275                 280                 285 caa tat gag ggg tct ctg act aca ccg ccc tgt gcc cag ggt gtc atc       912
Gln Tyr Glu Gly Ser Leu Thr Thr Pro Pro Cys Ala Gln Gly Val Ile
        290                 295                 300 tgg act gtg ttt aac cag aca gtg atg ctg agt gct aag cag ctc cac       960
Trp Thr Val Phe Asn Gln Thr Val Met Leu Ser Ala Lys Gln Leu His
305                 310                 315                 320 acc ctc tct gac acc ctg tgg gga cct ggt gac tct cgg cta cag ctg      1008
Thr Leu Ser Asp Thr Leu Trp Gly Pro Gly Asp Ser Arg Leu Gln Leu
                325                 330                 335 aac ttc cga gcg acg cag cct ttg aat ggg cga gtg att gag gcc tcc      1056
Asn Phe Arg Ala Thr Gln Pro Leu Asn Gly Arg Val Ile Glu Ala Ser
            340                 345                 350 ttc cct gct gga gtg gac agc agt cct cgg gct gct gag cca gtc cag      1104
Phe Pro Ala Gly Val Asp Ser Ser Pro Arg Ala Ala Glu Pro Val Gln
        355                 360                 365 ctg aat tcc tgc ctg gct gct ggt gac atc cta gcc ctg gtt ttt ggc      1152
Leu Asn Ser Cys Leu Ala Ala Gly Asp Ile Leu Ala Leu Val Phe Gly
370                 375                 380 ctc ctt ttt gct gtc acc agc gtc gcg ttc ctt gtg cag atg aga agg      1200
Leu Leu Phe Ala Val Thr Ser Val Ala Phe Leu Val Gln Met Arg Arg
385                 390                 395                 400 cag cac aga agg gga acc aaa ggg ggt gtg agc tac cgc cca gca gag      1248
Gln His Arg Arg Gly Thr Lys Gly Gly Val Ser Tyr Arg Pro Ala Glu
                405                 410                 415 gta gcc gag act gga gcc tagaggctgg atcttggaga atgtgagaag             1296
Val Ala Glu Thr Gly Ala
                420 ccagccagag gcatctgagg gggagccggt aactgtcctg tcctgctcat tatgccactt    1356 ccttttaact gccaagaaat tttttaaaat aaatatttat aat                      1399

<210> SEQ ID NO 2
<211> LENGTH: 422
<212> TYPE: PRT
<213> ORGANISM: Human

<400> SEQUENCE: 2

Gln Arg Leu Pro Arg Met Gln Glu Asp Ser Pro Leu Gly Gly Gly Ser
  1               5                  10                  15

Ser Gly Glu Asp Asp Pro Leu Gly Glu Glu Asp Leu Pro Ser Glu Glu
                 20                  25                  30

Asp Ser Pro Arg Glu Glu Asp Pro Pro Gly Glu Glu Asp Leu Pro Gly
             35                  40                  45

Glu Glu Asp Leu Pro Gly Glu Glu Asp Leu Pro Glu Val Lys Pro Lys
         50                  55                  60

Ser Glu Glu Glu Gly Ser Leu Lys Leu Glu Asp Leu Pro Thr Val Glu
 65                  70                  75                  80

Ala Pro Gly Asp Pro Gln Glu Pro Gln Asn Asn Ala His Arg Asp Lys
                 85                  90                  95

Glu Gly Asp Asp Gln Ser His Trp Arg Tyr Gly Gly Asp Pro Pro Trp
            100                 105                 110

Pro Arg Val Ser Pro Ala Cys Ala Gly Arg Phe Gln Ser Pro Val Asp
        115                 120                 125

Ile Arg Pro Gln Leu Ala Ala Phe Cys Pro Ala Leu Arg Pro Leu Glu
```

```
                130             135             140
Leu Leu Gly Phe Gln Leu Pro Pro Leu Pro Glu Arg Leu Arg Asn
145                 150                 155                 160

Asn Gly His Ser Val Gln Leu Thr Leu Pro Pro Gly Leu Glu Met Ala
                165                 170                 175

Leu Gly Pro Gly Arg Glu Tyr Arg Ala Leu Gln Leu His Leu His Trp
                180                 185                 190

Gly Ala Ala Gly Arg Pro Gly Ser Glu His Thr Val Glu Gly His Arg
                195                 200                 205

Phe Pro Ala Glu Ile His Val Val His Leu Ser Thr Ala Phe Ala Arg
                210                 215                 220

Val Asp Glu Ala Leu Gly Arg Pro Gly Gly Leu Ala Val Leu Ala Ala
225                 230                 235                 240

Phe Leu Glu Glu Gly Pro Glu Glu Asn Ser Ala Tyr Glu Gln Leu Leu
                245                 250                 255

Ser Arg Leu Glu Glu Ile Ala Glu Glu Gly Ser Glu Thr Gln Val Pro
                260                 265                 270

Gly Leu Asp Ile Ser Ala Leu Leu Pro Ser Asp Phe Ser Arg Tyr Phe
                275                 280                 285

Gln Tyr Glu Gly Ser Leu Thr Thr Pro Pro Cys Ala Gln Gly Val Ile
                290                 295                 300

Trp Thr Val Phe Asn Gln Thr Val Met Leu Ser Ala Lys Gln Leu His
305                 310                 315                 320

Thr Leu Ser Asp Thr Leu Trp Gly Pro Gly Asp Ser Arg Leu Gln Leu
                325                 330                 335

Asn Phe Arg Ala Thr Gln Pro Leu Asn Gly Arg Val Ile Glu Ala Ser
                340                 345                 350

Phe Pro Ala Gly Val Asp Ser Ser Pro Arg Ala Ala Glu Pro Val Gln
                355                 360                 365

Leu Asn Ser Cys Leu Ala Ala Gly Asp Ile Leu Ala Leu Val Phe Gly
                370                 375                 380

Leu Leu Phe Ala Val Thr Ser Val Ala Phe Leu Val Gln Met Arg Arg
385                 390                 395                 400

Gln His Arg Arg Gly Thr Lys Gly Gly Val Ser Tyr Arg Pro Ala Glu
                405                 410                 415

Val Ala Glu Thr Gly Ala
                420

<210> SEQ ID NO 3
<211> LENGTH: 29
<212> TYPE: DNA
<213> ORGANISM: HUMAN

<400> SEQUENCE: 3
cgcccagtgg gtcatcttcc ccagaagag                                    29

<210> SEQ ID NO 4
<211> LENGTH: 19
<212> TYPE: DNA
<213> ORGANISM: HUMAN

<400> SEQUENCE: 4
ggaatcctcc tgcatccgg                                               19
```

METHODS OF IMAGING NEOPLASTIC DISEASE AND OF DETECTING AND QUANTIFYING MN PROTEIN/ POLYPEPTIDE USING MN-SPECIFIC ANTIBODIES

This application is a continuation of U.S. Ser. No. 07/964,589, filed Oct. 21, 1992, which was issued as U.S. Pat. No. 5,387,676 on Feb. 7, 1995, and priority therefrom is declared under 35 USC 120. Priority is also declared under 35 USC Section 119 from now pending Czechoslovakian patent application PV-709-92 filed Mar. 11, 1992.

FIELD OF THE INVENTION

The present invention is in the general area of medical genetics and in the fields of biochemical engineering and immunochemistry. More specifically, it relates to the identification of a new gene—the MN gene—a cellular gene coding for the MN protein. The inventors hereof found MN proteins to be associated with tumorigenicity. Identification of MN antigen as well as antibodies specific therefor in patient samples provides the basis for diagnostic/prognostic assays for cancer.

BACKGROUND OF THE INVENTION

MaTu is a novel quasi-viral agent with rather unusual properties [Zavada, J., *Arch. Virol.* 50: 1–10 (1976)]. It is presumably derived from a human mammary tumor. In some respects, it resembles classical viruses whereas in other respects, it resembles "slow" viruses (prions), and in still other respects it is different from both classes of viruses.

MaTu was first detected by its capacity to complement mutants of vesicular stomatitis virus (VSV) with heat-labile surface G protein in HeLa cells (cell line derived from human cervical adenocarcinoma), which had been cocultivated with human breast carcinoma cells. The complementation resulted in the formation of phenotypically mixed virions—the VSV(MaTu) pseudotypes [Zavada et al., *Nature New Biol.* 240: 124–125 (1972)]. The virions contain the VSV genome, which is responsible for their ability to produce plaques (as well as internal VSV proteins), but the surface protein, corresponding to MaTu, determines their host range and neutralization specificities.

One of the paradoxical features of the MaTu agent is its host range. VSV(MaTu) is infectious only for human fibroblasts, but not for HeLa; however, the MaTu agent, detected by its capacity to donate surface protein for the VSV(MaTu) pseudotypes, is transmissible only to HeLa, but not to fibroblasts [Zavada et al., *J. Gen. Virol.*, 24: 327–337 (1974)].

By its complementation of VSV mutants and by its formation of pseudotypes, MaTu resembles known enveloped viruses. However, MaTu is transmissible only by direct cell-to-cell contact, and not by cell-free filtrates, thus differing from both classical and "slow" viruses. Its only permissive host appears to be HeLa cells. In those cells, MaTu spreads extremely slowly, and does not form morphologically distinct virions, thus resembling the "slow" viruses. [Zavada et al., (1974); Zavada and Zavadova, *Arch. Virol.* 118: 189–197 (1991)]. No known virus has HeLa cells as an exclusive host.

Since the above-described properties suggest that MaTu might be an entirely new type of molecular parasite of living cells, and since it possibly originated from a human tumor, there was a significant medical research interest to characterize it in more detail. Herein elucidated is the biological and molecular nature of MaTu. MaTu was found to be a two-component system, having an exogenous transmissible component, MX, and an endogenous cellular component, MN. The MN gene was further found to be present in the chromosomal DNA of all vertebrates tested, and its expression was found to be strongly correlated with tumorigenicity.

Described herein is the cloning and sequencing of the MN gene and the production of a MN-encoded protein in a bacterial vector. That genetically engineered MN protein as well as other MN proteins/polypeptides, can be used in serological assays according to this invention to detect MN-specific antibodies. Further, such MN proteins/polypeptides and antibodies reactive with MN antigen can be used in immunoassays according to this invention to detect and/or quantitate MN antigen. Such assays may be diagnostic and/or prognostic for neoplastic and/or pre-neoplastic disease.

SUMMARY OF THE INVENTION

Herein disclosed is the MN gene, a cellular gene which is the endogenous component of the MaTu agent. Substantially the entire cDNA sequence for the apparently intronless gene is shown in FIGS. 1A–B.

This invention is directed to said MN gene, fragments thereof and the related cDNA which are useful, for example, as follows: 1) to produce MN proteins/polypeptides by biochemical engineering; 2) to prepare nucleic acid probes to test for the presence of the MN gene in cells of a subject: 3) to prepare appropriate polymerase chain reaction (PCR) primers for use, for example, in PCR-based assays or to produce nucleic acid probes; 4) to identify MN proteins and polypeptides as well as homologs or near homologs thereto; 5) to identify various mRNAs transcribed from MN genes in various tissues and cell lines, preferably human; and 6) to identify mutations in MN genes. The invention further concerns purified and isolated DNA molecules comprising the MN gene or fragments, thereof, or the related cDNA or fragments thereof.

The invention further concerns the discovery of a hitherto unknown protein—MN, encoded by the MN gene. The expression of MN proteins is inducible by growing cells in dense cultures, and such expression was discovered to be associated with tumorigenic cells.

MN proteins were found to be produced by some human tumor cell lines in vitro, for example, by HeLa (cervical carcinoma), T24 (bladder carcinoma) and T47D (mammary carcinoma) and SK-Mel 1477 (melanoma) cell lines, by tumorigenic hybrid cells and by cells of some human cancers in vivo, for example, by cells of uterine cervical, ovarian and endometrial carcinomas as well as cells of some benign neoplasias such as mammary papillomas. MN proteins were not found in non-tumorigenic hybrid cells or in the cells of normal tissues. Thus, MN proteins are considered to be tumor-specific.

In HeLa and in tumorigenic HeLa x fibroblast hybrid (H/F/T) cells, MN protein is manifested as a "twin" protein p54/58N; it is glycosylated and forms disulfide-linked oligomers. As determined by electrophoresis upon reducing gels, MN proteins have molecular weights in the range of from about 40 kd to about 70 kd, preferably from about 45 kd to about 65 kd, more preferably from about 48 kd to about 58 kd. Upon non-reducing gels, MN proteins in the form of oligomers have a molecular weights in the range of from about 145 kd to about 160 kd, preferably from about 150 to about 155 kd, still more preferably from about 152 to about 154 kd. The predicted amino acid sequence for a preferred MN protein of this invention is shown in FIG. 1A–1B.

The discovery of the MN gene and protein and thus, of substantially complementary MN genes and proteins encoded thereby, led to the finding that the expression of MN proteins was associated with tumorigenicity. That finding resulted in the creation of methods that are diagnostic/prognostic for cancer and precancerous conditions. Methods and compositions are provided for identifying the onset and presence of neoplastic disease by detecting and/or quantitating MN antigen in patient samples, including cell and tissue extracts from vertebrates, preferably mammals and more preferably humans. Such MN antigen may also be found in body fluids.

MN proteins and genes are of use in research concerning the molecular mechanisms of oncogenesis, in cancer diagnostics/prognostics, and may be of use in cancer immunotherapy.

The present invention is useful for detecting a wide variety of neoplastic and/or pre-neoplastic diseases. Exemplary neoplastic diseases include carcinomas, such as mammary, bladder, ovarian, uterine, cervical, endometrial, squamous cell and adenosquamous carcinomas; and head and neck cancers; mesodermal tumors, such as neuroblastomas and retinoblastomas; sarcomas, such as osteosarcomas and Ewing's sarcoma; and melanomas. Of particular interest are head and neck cancers, gynecologic cancers including ovarian, cervical, vaginal, endometrial and vulval cancers; gastrointestinal cancer, such as, stomach, colon and esophageal cancers; urinary tract cancer, such as, bladder and kidney cancers; skin cancer; liver cancer; prostate cancer; lung cancer; and breast cancer. Of still further particular interest are gynecologic cancers; breast cancer; urinary tract cancers, especially bladder cancer; lung cancer; gastrointestinal cancer, such as, stomach, colon and esophageal cancers; and liver cancer. Even further of particular interest are gynecologic cancers and breast cancer. Gynecologic cancers of particular interest are carcinomas of the uterine cervix, endometrium and ovaries; more particularly such gynecologic cancers include cervical squamous cell carcinomas, adenosquamous carcinomas, adenocarcinomas as well as gynecologic precancerous conditions, such as metaplastic cervical tissues and condylomas.

The invention further relates to the biochemical engineering of the MN gene, fragments thereof or related cDNA. For example, said gene or a fragment thereof or related cDNA can be inserted into a suitable expression vector; host cells can be transformed with such an expression vector; and an MN protein/polypeptide, preferably an MN protein, is expressed therein. Such a recombinant protein or polypeptide can be glycosylated or nonglycosylated, preferably glycosylated, and can be purified to substantial purity. The invention further concerns MN proteins/polypeptides which are synthetically or otherwise biologically prepared.

Said MN proteins/polypeptides can be used in assays to detect MN antigen in patient samples and in serological assays to test for MN-specific antibodies. MN proteins/polypeptides of this invention are serologically active, immunogenic and/or antigenic. They can further be used as immunogens to produce MN-specific antibodies, polyclonal and/or monoclonal, as well as an immune T-cell response.

The invention further is directed to MN-specific antibodies, which can be used diagnostically/prognostically and may be used therapeutically. MN-specific antibodies can be used, for example, in laboratory diagnostics, using immunofluorescence microscopy or immunohistochemical staining; as a component in immunoassays for detecting and/or quantitating MN antigen in, for example, clinical samples; as probes for immunoblotting to detect MN antigen; in immunoelectron microscopy with colloid gold beads for localization of MN proteins and/or polypeptides in cells; and in genetic engineering for cloning the MN gene or fragments thereof, or related cDNA. Such MN-specific antibodies can be used as components of diagnostic/prognostic kits, for example, for in vitro use on histological sections; such antibodies can also and used for in vivo diagnostics/prognostics, for example, such antibodies can be labeled appropriately, as with a suitable radioactive isotope, and used in vivo to locate metastases by scintigraphy. Further such antibodies may be used in vivo therapeutically to treat cancer patients with or without toxic and/or cytostatic agents attached thereto. Further, such antibodies can be used in vivo to detect the presence of neoplastic and/or pre-neoplastic disease. Still further, such antibodies can be used to affinity purify MN proteins and polypeptides.

A hybridoma that produces a representative MN-specific antibody, the monoclonal antibody M75, was deposited at the American Type Culture Collection [ATCC; 10801 University Blvd., Manassas, Va. 20110-2209 (USA)] on Sep. 17, 1992, under ATCC Number HB 11128. The M75 antibody was used to discover and identify the MN protein and can be used to readily identify MN antigen in Western blots, in radioimmunoassays and immunohistochemically, for example, in tissue samples that have been formalin fixed.

This invention also concerns recombinant DNA molecules comprising a DNA sequence that encodes for an MN protein or polypeptide, and also recombinant DNA molecules that encode not only for an MN protein or polypeptide but also for an amino acid sequence of a non-MN protein/polypeptide, preferably which is not immunogenic to humans and which is not typically reactive to antibodies in human body fluids. Examples of such a DNA sequence is the alpha-peptide coding region of beta-galactosidase and a sequence coding for glutathione S-transferase or a fragment thereof. Further, claimed herein are such recombinant fusion proteins/polypeptides which are substantially pure and non-naturally occurring. An exemplary fusion protein of this invention is pGEX-3X-MN.

This invention also concerns methods of treating neoplastic disease and/or pre-neoplastic disease comprising inhibiting the expression of MN genes by administering antisense nucleic acid sequences that are substantially complementary to mRNA transcribed from MN genes. Preferred are antisense nucleic acid sequences that are substantially complementary to sequences at the 5' end of the MN cDNA sequence shown in FIGS. 1A–1B. Preferably said antisense nucleic acid sequences are oligonucleotides.

This invention also concerns vaccines comprising an immunogenic amount of one or more substantially pure MN proteins and/or polypeptides dispersed in a physiologically acceptable, nontoxic vehicle, which amount is effective to immunize a vertebrate, preferably a mammal, more preferably a human, against a neoplastic disease associated with the expression of MN proteins. Said proteins can be recombinantly, synthetically or otherwise biologically produced. Recombinent MN proteins includes fusion proteins, as exemplified by pGEX-3X-MN. A-particular use of said vaccine would be to prevent recidivism and/or metastasis. For example, it could be administered to a patient who has had an MN-carrying tumor surgically removed, to prevent recurrence of the tumor.

The invention still further concerns nucleic acid probes that are substantially complementary to nucleic acid sequences of the MN gene. Preferred nucleic acid probes of this invention are those with sequences substantially complementary to sequences from the MN cDNA shown in FIG. 1A–1B. Test kits of this invention can comprise such probes which are useful diagnostically/prognostically for neoplastic and/or pre-neoplastic disease. Preferred test kits comprise means for detecting or measuring the hybridization of said probes to the MN gene or to the mRNA product of the MN gene, such as a visualizing means.

The immunoassays of this invention can be embodied in test kits which comprise MN proteins/polypeptides and/or MN-specific antibodies. Such test kits can be in solid phase formats, but are not limited thereto, and can also be in liquid phase format, and can be based on ELISAS, particle assays, radiometric or fluorometric assays either unamplified or amplified, using, for example, avidin/biotin technology.

Abbreviations

The following abbreviations are used herein:
AA—amino acid
ATCC—American Type Culture Collection
bp—base pairs
BSA—bovine serum albumin
Ci—curie
cm—centimeter
cpm—counts per minute
C-terminus—carboxyl-terminus
°C.—degrees centigrade
DMEM—Dulbecco modified Eagle medium
EDTA—ethylenediaminetetracetate
EIA—enzyme immunoassay
ELISA—enzyme-linked immunosorbent assay
F—fibroblasts
FCS—fetal calf serum
FIBR—fibroblasts
FITC—fluorescein isothiocyanate
H—HeLa cells
HEF—human embryo fibroblasts
HeLa K—standard type of HeLa cells
HeLa S—Stanbridge's mutant HeLa D98/AH.2
H/F-T—hybrid HeLa fibroblast cells that are tumorigenic; derived from HeLa D98/AH.2
H/F-N—hybrid HeLa fibroblast cells that are nontumorigenic; derived from HeLa D98/AH.2
HGPRT$^-$—hypoxanthine guanine phosphoribosyl transferase-deficient
HRP—horseradish peroxidase
IPTG—isopropyl-Beta-D-thiogalacto-pyranoside
kb—kilobase
kd—kilodaltons
M—molar
mA—milliampere
MAb—monoclonal antibody
ME—mercaptoethanol
MEM—minimal essential medium
mg—milligram
ml—milliliter
mM—millimolar
MTV—mammary tumor virus
N—normal concentration
ng—nanogram
N-terminus—amino-terminus
ODN—oligodeoxynucleotide
PAGE—polyacrylamide gel electrophoresis
PBS—phosphate buffered saline
PEST—combination of one-letter abbreviations for proline, glutamic acid, serine, threonine
pI—isoelectric point
RIP—radioimmunoprecipitation
RIPA—radioimmunoprecipitation assay
SAC—protein A-*Staphylococcus aureus* cells
SDS—sodium dodecyl sulfate
SDS-PAGE—sodium dodecyl sulfate-polyacrylamide gel electrophoresis
SSPE—NaCl (0.18 M), sodium phosphate (0.01 M), EDTA (0.001 M)
TCA—trichloroacetic acid
TC media—tissue culture media
$\mu$ci—microcurie
$\mu$g—microgram
$\mu$l —microliter
$\mu$M—micromolar
VSV—vesicular stomatitis virus
X-MLV—xenotropic murine leukemia virus Cell Lines The following cell lines were used in the experiments herein described:

HeLa K—standard type of HeLa cells; aneuploid, epithelial-like cell line isolated from a human cervical adenocarcinoma [Gey et al., *Cancer Res.*, 12: 264 (1952); Jones et al., *Obstet. Gynecol.*, 38: 945–949 (1971)] obtained from Professor B. Korych, [Institute of Medical Microbiology and Immunology, Charles University; Prague, Czechoslovakia]

HeLa D98/AH.2 (also HeLa S)—Mutant HeLa clone that is hypoxanthine guanine phosphoribosyl transferase-deficient (HGPRT$^-$) kindly provided by Eric J. Stanbridge [Department of Microbiology, College of Medicine, University of California, Irvine, Calif. (USA)] and reported in Stanbridge et al., *Science,* 215: 252–259 (Jan. 15, 1982); parent of hybrid cells H/F-N and H/F-T, also obtained from E. J. Stanbridge.

NIH-3T3—murine fibroblast cell line reported in Aaronson, *Science,* 237: 178 (1987).

T47D—cell line derived from a human mammary carcinoma [Keydar et al., *Eur. J. Cancer.* 15: 659–670 (1979)]; kindly provided by J. Keydar [Haddasah Medical School; Jerusalem, Israel]

T24—cell line from urinary bladder carcinoma [Bubenik et al., *Int. J. Cancer.* 11: 765–773 (1973)] kindly provided by J. Bubenik [Institute of Molecular Genetics, Czechoslovak Academy of Sciences; Prague, Czechoslovakia]

HMB2—cell line from melanoma [Svec et al., *Neoplasma,* 35: 665–681 (1988)]

HEF—human embryo fibroblasts [Zavada et al., *Nature New Biology,* 240: 124–125 (1972)]

SIRC—cell line from rabbit cornea (control and X-MLV-infected) [Zavada et al., *Virology,* 82: 221–231 (1977)]

Vero cells—African green monkey cell line [Zavada et al. (1977)]

myeloma cell line NS-0—myeloma cell line used as a fusion parent in production of monoclonal antibodies [Galfre and Milstein, *Methods Enzymol*, 73: 3–46 (1981)]

SK-Mel 1477—human melanoma cell line kindly provided by K. E. Hellstrom [Division of Tumor Immunology, Fred Hutchins Cancer Research Center; Seattle, Washington (USA)]

XC—cells derived from a a rat rhabdomyosarcoma induced with Rous sarcoma virus-induced rat sarcoma [Svoboda, J., *Natl. Cancer Center Institute Monograph No.* 17, IN: "International Conference on Avian Tumor Viruses" (J. W. Beard ed.), pp. 277–298 (1964)], kindly provided by Jan Svoboda [Institute of Molecular Genetics, Czechoslovak Academy of Sciences; Prague, Czechoslovakia]; and Rat 2-Tk⁻—a thymidine kinase deficient cell line, kindly provided by L. Kutinova [Institute of Sera and Vaccines; Prague, Czechoslovakia]

CGL1—H/F-N hybrid cells (HeLa D98/AH.2 derivative)
CGL2—H/F-T hybrid cells (HeLa D98/AH.2 derivative)
CGL3—H/F-T hybrid cells (HeLa D98/AH.2 derivative)
CGL4—H/F-T hybrid cells (HeLa D98/Ah.2 derivative)

Nucleotide and Amino Acid Sequence Symbols

The following symbols are used to represent nucleotides herein:

| Base | Symbol |
| --- | --- |
| adenine | A |
| cytosine | C |
| guanine | G |
| thymine | T |
| uracil | U |

There are twenty main amino acids, each of which is specified by a different arrangement of three adjacent nucleotides (triplet code or codon), and which are linked together in a specific order to form a characteristic protein. A three-letter convention is used herein to identify said amino acids, as, for example, in FIGS. 1A–B, as follows:

| Amino acid name | Symbol |
| --- | --- |
| Alanine | Ala |
| Arginine | Arg |
| Asparagine | Asn |
| Aspartic Acid | Asp |
| Cysteine | Cys |
| Glutamic Acid | Glu |
| Glutamine | Gln |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |

BRIEF DESCRIPTION OF THE FIGURES

FIGS. 1A–1B provides the nucleotide sequence for the MN cDNA clone isolated as described herein and the predicted amino acid sequence encoded by the cDNA [SEQ. ID. NOS.: 1 and 2, respectively]. That sequence data has been sent to the EMBL Data Library in Heidelberg, Germany and is available under Accession No. X66839.

FIG. 2 provides SDS-PAGE and immunoblotting analyses of recombinant MN protein expressed from a pGEX-3X bacterial expression vector. Two parallel samples of purified recombinant MN protein (twenty μg in each sample) were separated by SDS-PAGE on a 10% gel. One sample (A in FIG. 2) was stained with Coomassie brilliant blue; whereas the other sample (B) was blotted onto a Hybond C membrane [Amersham; Aylesbury, Bucks, England]. The blot was developed by autoradiography with $^{125}$I-labeled Mab M75.

FIG. 3 illustrates inhibition of p54/58 expression by antisense oligodeoxynucleotides (ODNs). HeLa cells cultured in overcrowded conditions were incubated with (A) 29-mer ODNI; [SEQ. ID. NO.:3] (B) 19-mer ODN2; [SEQ. ID. NO.:4] (C) both ODNI and ODN2; and (D) without ODNS. Example 11 provides details of the procedures used.

FIG. 4 shows the results of Northern blotting of MN mRNA in human cell lines. Total RNA was prepared from the following cell lines: HeLa cells growing in dense (A) and sparse (B) culture; (C) H/F-N; (D) and (E) H/F-T; and (F) human embryo fibroblasts. Example 12 details the procedure and results.

FIG. 5 illustrates the detection of the MN gene on genomic DNAs by Southern blotting. Chromosomal DNA digested by SstI was as follows: (A) chicken; (B) bovine; (C) feline; (D) MX-infected HeLa cells; (E) mouse NIH-3T3 cells; (F) human placental cells; (G) HeLa cells; (H) sheep; (I) human melanoma cells; and (J) monkey Vero cells. The procedures used are detailed in Example 13.

FIGS. 6A–B graphically illustrates the expression of MN- and MX-specific proteins in human fibroblasts (F), in HeLa cells (H) and in H/F-N and H/F-T hybrid cells and contrasts the expression in MX-infected and MX-uninfected cells. Example 5 details the procedures and results.

FIG. 7 (discussed in Example 5) provides immunoblots of MN proteins in fibroblasts (FIBR) and in HeLa K, HeLa S, H/F-N and H/F-T hybrid cells.

FIG. 8 (discussed in Example 6) shows immunoblots of MN proteins in cell culture extracts prepared from the following: (A) MX-infected HeLa cells; (B) human fibroblasts; (C) T24; (D) T47D; (E) SK-Mel 1477; and (F) HeLa cells uninfected with MX. The symbols +ME and O ME indicate that the proteins were separated by PAGE after heating in a sample buffer, with and without 3% mercaptoethanol (ME), respectively.

FIG. 9 (discussed in Example 6) provides immunoblots of MN proteins from human tissue extracts. The extracts were prepared from the following: (A) MX-infected HeLa cells; (B) full-term placenta; (C) corpus uteri; (D, M) adenocarcinoma endometrii; (E, N) carcinoma ovarii; (F, G) trophoblasts; (H) normal ovary; (I) myoma uteri; (J) mammary papilloma; (K) normal mammary gland; (L) hyperplastic endometrium; (O) cervical carcinoma; and (P) melanoma.

FIG. 10 (discussed in example 7) provides immunoblots of MN proteins from (A) MX-infected HeLa cells and from (B) Rat2-Tk⁻cells. (+ME and O ME have the same meanings as explained in the legend to FIG. 8.)

FIGS. 11A–B (discussed in Example 8) graphically illustrates the results from radioimmunoprecipitation experiments with $^{125}$I-pGEX-3X-MN protein and different antibodies. The radioactive protein (15×10³ cpm/tube) was precipitated with ascitic fluid or sera and SAC as follows: (A) ascites with MAb M75; (B) rabbit anti-MaTu serum; (C) normal rabbit serum; (D) human serum L8; (E) human serum KH; and (F) human serum M7.

FIG. 12 (discussed in Example 8) shows the results from radioimmunoassays for MN antigen. Ascitic fluid (dilution precipitating 50% radioactivity) was allowed to react for 2 hours with (A) "cold" (unlabeled) protein pGEX-3X-MN, or with extracts from cells as follows: (B) HeLa+MX; (C) Rat-2Tk⁻; (D) HeLa; (E) rat XC; (F) T24; and (G) HEF. Subsequently $^{125}$I-labeled pGEX-3X-MN protein ($25 \times 10^3$ cpm/tube) was added and incubated for an additional 2 hours. Finally, the radioactivity to MAb M75 was adsorbed to SAC and measured.

FIGS. 13A–F (discussed in Example 10) provides results of immunoelectron and scanning microscopy of MX-uninfected (control) and MX-infected HeLa cells. Panels A–D show ultrathin sections of cells stained with MAb M75 and immunogold; Panels E and F are scanning electron micrographs of cells wherein no immunogold was used. Panels E and F both show a terminal phase of cell division. Panels A and E are of control HeLa cells; panels B, C, D and F are of MX-infected HeLa cells. The cells shown in Panels A, B and C were fixed and treated with M75 and immunogold before they were embedded and sectioned. Such a procedure allows for immunogold decoration only of cell surface antigens. The cells in Panel D were treated with M75 and immunogold only once they had been embedded and sectioned, and thus antigens inside the cells could also be decorated.

DETAILED DESCRIPTION

MaTu—MX and MN Components

As demonstrated herein MaTu is a two-component system. One part of the complex, exogenous MX, is transmissible, and is manifested by a protein, p58X, which is a cytoplasmic antigen which reacts with some natural sera, of humans and of various animals. The other component, MN, is endogenous to human cells.

MN is a cellular gene, showing only very little homology with known DNA sequences. It is rather conservative and is present as a single copy gene in the chromosomal DNA of various vertebrates. Described herein is the cloning and sequencing of the MN cDNA, and the genetic engineering of a fusion protein, namely MN plus the carboxyl terminus of glutathione S-transferase, that can be conveniently purified by affinity chromatography.

MN is manifested in HeLa cells by a twin protein(s), p54/58N, that is localized on the cell surface and in the nucleus. Immunoblots using a monoclonal antibody reactive with p54/58N (MAb M75) revealed two bands at 54 kd and 58 kd. Those two bands may correspond to one type of protein that differs by glycosylation pattern or by how it is processed. (Both p54N and p58N are glycosylated with oligosaccharidic residues containing mannose, but only p58N also contains glucosamine.) Herein, the phrase "twin protein" indicates p54/58N.

MN is absent in rapidly growing, sparse cultures of HeLa, but is inducible either by keeping the cells in dense cultures or, more efficiently, by infecting them with MX. Those inducing factors are synergistic. Only p54/58N is associated with virions of vesicular stomatitis virus (VSV), reproduced in MaTu-infected HeLa. Whereas the twin protein p54/58N is glycosylated and forms oligomers linked by disulfidic bonds, p58X is not glycosylated and does not form S-S-linked oligomers.

VSV assembles p54/58N into virions in HeLa cells, indicating that the twin protein is responsible for complementation of VSV G-protein mutants and for formation of VSV(MaTu) pseudotypes. As only enveloped viruses provide surface glycoproteins for the formation of infectious, functioning pseudotypes, which can perform such specific functions as adsorption and penetration of virions into cells [Zavada, J., *J. Gen. Virol.,* 63: 15–24 (1982)], that observation implies that the MN gene behaves as a quasi-viral sequence.

The surface proteins of enveloped viruses, which participate in the formation of VSV pseudotypes, are glycosylated as is the MN twin protein, p54/58N. MN proteins also resemble viral glycoproteins in the formation of oligomers (preferably tri- or tetramers); such oligomerization, although not necessarily involving S-S bonds (disulfidic bonds), is essential for the assembly of virions [Kreis and Lodish, *Cell,* 46: 929–937 (1986)]. The disulfidic bonds can be disrupted by reduction with 2-mercaptoethanol.

As reported in Pastorekova et al., *Virology,* 187: 620–626 (1992), after reduction with mercaptoethanol, p54/58N from cell extracts or from VSV looks very similar on immunoblot. Without reduction, in cell extracts, it gives several bands around 150 kd, suggesting that the cells may contain several different oligomers (probably with a different p54:p58 ratio), but VSV selectively assembles only one of them, with a molecular weight of about 153 kd. That oligomer might be a trimer, or rather a tetramer, consisting of 54 kd and 58 kd proteins. The equimolar ratio of p54:p58 in VSV virions is indicated by approximately the same strength of 54 kd and 58 kd bands in a VSV sample analyzed under reducing conditions.

The expression of MN proteins appears to be diagnostic/prognostic for neoplastic disease. The MN twin protein, p54/58N, was found to be expressed in HeLa cells and in Stanbridge's tumorigenic (H/F-T) hybrid cells [Stanbridge et al., *Somatic Cell Genet.* 7: 699–712 (1981); and Stanbridge et al., *Science,* 215: 252–259 (1982)] but not in fibroblasts or in non-tumorigenic (H/F-N) hybrid cells [Stanbridge et al., id.] MN proteins were found in immunoblots prepared from human ovarian, endometrial and uterine cervical carcinomas, and in some benign neoplasias (as mammary papilloma) but not from normal ovarian, endometrial, uterine or placental tissues. In HeLa cells infected with MX, observed were conspicuous ultrastructural alterations, that is, the formation of abundant filaments on cell surfaces and the amplification of mitochondria. Using an immunogold technique, p54/58N was visualized on the surface filaments and in the nucleus, particularly in the nucleoli. Thus MN proteins appear to be tumor-specific as they do not appear to be produced by normal non-tumor cells.

The examples herein show that MX and MN are two different entities, that can exist independently of each other. MX as an exogenous, transmissible agent can multiply in fibroblasts and in H/F-N hybrid cells which are not expressing MN-related proteins (FIG. 6). In such cells, MX does not induce the production of MN protein. MN protein can be produced in HeLa and other tumor cells even in the absence of MX as shown in FIGS. 6–9. However, MX is a potent inducer of MN-related protein in HeLa cells; it increases its production thirty times over the concentration observed in uninfected cells (FIGS. 7 and 12, Table 1 in Example 8, below).

MN Gene—Cloning and Sequencing

FIGS. 1A–1B provides the nucleotide sequence for the MN cDNA clone isolated as described within this section. It is understood that because of the degeneracy of the genetic code, that is, that more than one codon will code for one amino acid [for example, the codons TTA, TTG, CTT, CTC, CTA and CTG each code for the amino acid leucine (leu)], that variations of the nucleotide sequence in, for example, FIGS. 1A–B, wherein one codon is substituted for another, would produce a substantially equivalent protein or polypeptide according to this invention. All such variations in the nucleotide sequence of the MN cDNA and complementary nucleic acid sequences are included within the scope of this invention.

It is further understood that the nucleotide sequence herein described and shown in FIGS. 1A–1B represents only the precise structure of the cDNA nucleotide sequence isolated and described herein. It is expected that slightly modified nucleotide sequences will be found or can be modified by techniques known in the art to code for substantially similar MN proteins and polypeptides, for example, those having similar epitopes, and such nucleotide sequences and proteins/polypeptides are considered to be equivalents for the purpose of this invention. DNA or RNA having equivalent codons is considered within the scope of the invention, as are synthetic nucleic acid sequences that encode proteins/polypeptides homologous or substantially homologous to MN proteins/polypeptides, as well as those nucleic acid sequences but for the degeneracy of the genetic code would hybridize to said cDNA nucleotide sequence. Modifications and variations of nucleic acid sequences as indicated herein are considered to result in sequences that are substantially the same as the MN sequence and fragments thereof.

To find the MN gene, a lambda gt11 cDNA library from MX-infected HeLa cells was prepared. Total RNA from MX-infected HeLa cells was isolated by a guanidinium-thiocyanate-CsCl method, and the mRNA was affinity separated on oligo dT-cellulose. The synthesis of the cDNA and its cloning into lambda gt11 was carried out using kits from Amersham, except that the EcoRI-NotI adaptor was from Stratagene [La Jolla, Calif. (USA)]. The library was subjected to immunoscreening with monoclonal antibody M75 in combination with goat anti-mouse antibodies conjugated with alkaline phosphatase. That immunoscreening method is described in Young and Davis, *PNAS (USA)*. 80: 1194–1198 (1983). One positive clone was picked from 350,000 screened plaques (representing about one-half of the whole library).

The positive clone was subcloned into the NotI site of pBluescript KS [Stratagene] thereby creating pBluescript-MN. Two oppositely oriented nested deletions were made using Erase-a-Base™ kit [Promega; Madison, Wis. (USA)] and sequenced by dideoxy method with a T7 sequencing kit [Pharmacia; Piscataway, N.J. (USA)]. The sequencing showed a partial cDNA clone, the insert being 1397 bp long. That sequence is shown in FIGS. 1A–1B. The sequence comprises a large 1290 bp open reading frame and 107 bp 3' untranslated region containing a polyadenylation signal (AATAAA). Another interesting feature of the sequence is the presence of a region contributing to instability of the mRNA (AUUUA at position 1389) which is characteristic for mRNAs of some oncogenes and lymphokines [Shaw and Kamen, *Cell,* 46: 659–667 (1986)]. As follows from a comparison of the size of the MN clone with that of the corresponding mRNA in a Northern blot (FIG. 4), the cDNA is missing about 100 bp from the 5' end of its sequence.

The open reading frame of MN cDNA clone encodes a putative protein of about 48 kd (FIG. 1). Analysis of the deduced translated amino acid (AA) sequence failed to show any significant homology to published protein sequences. The closest homology found was that of the C-terminal part of the MN protein and different types of carbonic anhydrase (about 30–35% in 170–200 AA overlap). The active site as well as the $Zn^{2+}$ binding domain of carbonic anhydrase are well-conserved in the MN protein. However, the MN gene is clearly a novel sequence derived from the human genome.

Although as indicated, the MN gene shows some homology with known carbonic anhydrases, it differs from them in several repects. Seven carbonic anhydrases are known [Dodgson et al. (eds.), *The Carbonic Anhydrases,* (Plenum Press; New York/London (1991)]. Each of their genes contains seven introns whereas the MN gene is apparently intronless. Also, all the known carbonic anhydrases are proteins of about 30 kd, smaller than the p54/58N-related products of the MN gene. Further, the carbonic anhydrases do not form oligomers as do the MN-related proteins.

From the predicted amino acid sequence, it is evident that the product of the MN gene is a basic protein (pI 9.08), with one potential N-glycosylation site located at the amino acid positions 303–313. Those observations correspond to the finding that p54/58N proteins from HeLa cells are sensitive to Endo H and Endo F cleavage, which causes a loss of about 3 kd each. The hydrophilicity profile reveals a hydrophobic sequence of amino acids (at positions 371–395) probably representing the region spanning the plasma membrane and containing also a potential cleavage signal. The profile fits well with the observation that p54/58N proteins are localized on the cell membrane. There are no PEST regions in the MN amino acid sequence, suggesting that the product of the MN gene is a stable long-lived protein [Rogers et al., *Science,* 234: 364–368 (1986)]. Such a feature explains our experience with inefficient metabolic labeling of p54/58N. The deduced amino acid sequence displays also other features namely, 10 potential phosphorylation and 7 myristylation sites, and 3 antigenic determinants.

To determine whether both p54/58N proteins were encoded by one gene, antisense ODNs were used to inhibit specifically MN gene expression. [Such use of antisense ODNs is reviewed in Stein and Cohen, *Cancer Res.,* 48: 2659–2668 (1988).] Those experiments are detailed in Example 11. The findings indicated that cultivation of HeLa cells with ODNs resulted in a considerable inhibition of p54/58N synthesis, whereas the amount of different HeLa cell proteins produced remained approximately the same. Further, and importantly on immunoblotting, the specific inhibition by ODNs affected both of the p54/58N proteins (FIG. 3). Thus, it was concluded that the MN gene that was cloned codes for both of the p54/58N proteins in HeLa cells.

To confirm whether the gene that was cloned codes for the p54/58N-specific protein, it was subcloned into the bacterial expression vector pGEX-3X [Pharmacia; Upsala, Sweden], constructed to express a fusion protein containing the C-terminus of glutathione S-transferase. That subcloning is representative of one method to genetically engineer an MN-related protein of this invention. The following description is exemplary and not meant to limit the invention in any way.

Production of Fusion Protein PGEX-3X-MN

The cDNA insert from the above-described pBluescript-MN was released by digesting the plasmid DNA by NotI. It was then treated with S1 nuclease to obtain blunt ends and then cloned into a dephosphorylated SmaI site of pGEX-3X (Pharmacia). After transformation of XL1-Blue cells and induction with IPTG, a fusion protein was obtained.

The fusion protein—MN glutathione S-transferase was purified by affinity chromatography on Glutathione-S-Sepharose 4B (Pharmacia). Twenty micrograms of the purified recombinant protein in each of two parallel samples were separated by SDS-PAGE on a 10% gel. One of the samples (A) was stained with Coomassie brilliant blue, whereas the other (B) was blotted onto a Hybond C membrane (Amersham). The blot was developed by autoradiography with $^{125}$I-labeled MAb M75. The results are shown in FIG. 2.

SDS-PAGE analysis provided an interesting result: a number of protein bands with different molecular weights (FIG. 2A). A similar SDS-PAGE pattern was obtained with another representative fusion protein produced according to this invention, beta-galactosidase-MN that was expressed from lambda gt11 lysogens. It appears that those patterns are due to translation errors caused by the presence of 9 AGGAGG codon tandems in the MN sequence. The use of those codons is strongly avoided in bacterial genes because of the shortage of corresponding tRNAs. Thus, during the translation of AGGAGG tandems from foreign mRNA, +1 ribosomal frameshifts arise with a high frequency (about 50%) [Spanjaard et al., *Nuc. Acid Res.*, 18: 5031–5036 (1990)].

By immunoblotting, a similar pattern was obtained: all the bands seen on stained SDS-PAGE gel reacted with the MN-specific MAb M75 (FIG. 2B), indicating that all the protein bands are MN-specific. Also, that result indicates that the binding site for MAb M75 is on the N-terminal part of the MN protein, which is not affected by frameshifts.

As shown in Example 8 below, the fusion protein pGEX-3X-MN was used in radioimmunoassays for MN-specific antibodies and for MN antigen.

MN Proteins and/or Polypeptides

The phrase "MN proteins and/or polypeptides" (MN proteins/polypeptides) is herein defined to mean proteins and/or polypeptides encoded by an MN gene or fragments thereof. An exemplary and preferred MN protein is that for which the predicted amino acid sequence is shown in FIG. 1A–1B. Preferred MN proteins/polypeptides are those proteins and/or polypeptides that have substantial homology with that MN protein shown in FIGS. 1A–1B.

A "polypeptide" is a chain of amino acids covalently bound by peptide linkages and is herein considered to be composed of 50 or less amino acids. A "protein" is herein defined to be a polypeptide composed of more than 50 amino acids.

It can be appreciated that a protein or polypeptide produced by a neoplastic cell in vivo could be altered in sequence from that produced by a tumor cell in cell culture. Thus, MN proteins and/or polypeptides which have varying amino acid sequences including without limitation, amino acid substitutions, extensions, deletions, truncations and combinations thereof, fall within the scope of this invention. It can also be appreciated that a protein extant within body fluids is subject to degradative processes, such as, proteolytic processes; thus, MN proteins that are significantly truncated and MN polypeptides may be found in body fluids, such as, sera. The phrase "MN antigen" is used herein to encompass MN proteins and/or polypeptides.

It will further be appreciated that the amino acid sequence of MN proteins and polypeptides can be modified by genetic techniques. One or more amino acids can be deleted or substituted. Such amino acid changes may not cause any measurable change in the biological activity of the protein or polypeptide and result in proteins or polypeptides which are within the scope of this invention.

The MN proteins and polypeptides of this invention can be prepared in a variety of ways according to this invention, for example, recombinantly, synthetically or otherwise biologically, that is, by cleaving longer proteins and polypeptides enzymatically and/or chemically. A preferred method to prepare MN proteins is by a recombinant means. A particularly preferred method of recombinantly producing a MN protein is described above for the fusion protein pGEX-3X-MN.

Recombinant Production of MN Proteins and Polypeptides

A representative method to prepare the MN protein shown in FIGS. 1A–1B or fragments thereof would be to insert the appropriate fragment of the MN cDNA into an appropriate expression vector as exemplified above. A wide variety of host-cloning vector combinations may be usefully employed in cloning the MN DNA isolated as described herein. For example, useful cloning vehicles may include chromosomal, nonchromosomal and synthetic DNA sequences such as various known bacterial plasmids such as pBR322, other *E. coli* plasmids and their derivatives and wider host range plasmids such as RP4, phage DNA, such as, the numerous derivatives of phage lambda, e.g., NB989 and vectors derived from combinations of plasmids and phage DNAs such as plasmids which have been modified to employ phage DNA expression control sequences. The plasmid pGEX-3X is a preferred cloning vehicle.

Useful hosts may be eukaryotic or prokaryotic and include bacterial hosts such as *E. coli* and other bacterial strains, yeasts and other fungi, animal or plant hosts such as animal or plant cells in culture, insect cells and other hosts. Of course, not all hosts may be equally efficient. The particular selection of host-cloning vehicle combination may be made by those of skill in the art after due consideration of the principles set forth herein without departing from the scope of this invention.

The particular site chosen for insertion of the selected DNA fragment into the cloning vehicle to form a recombinant DNA molecule is determined by a variety of factors. These include size and structure of the protein or polypeptide to be expressed, susceptibility of the desired protein or polypeptide to endoenzymatic degradation by the host cell components and contamination by its proteins, expression characteristics such as the location of start and stop codons, and other factors recognized by those of skill in the art.

The recombinant nucleic acid molecule containing the MN gene, fragment thereof, or cDNA therefrom, may be employed to transform a host so as to permit that host (transformant) to express the structural gene or fragment thereof and to produce the protein or polypeptide for which the hybrid DNA encodes. The recombinant nucleic acid molecule may also be employed to transform a host so as to permit that host on replication to produce additional recombinant nucleic acid molecules as a source of MN nucleic acid and fragments thereof. The selection of an appropriate host for either of those uses is controlled by a number of factors recognized in the art. These include, for example, compatibility with the chosen vector, toxicity of the co-products, ease of recovery of the desired protein or polypeptide, expression characteristics, biosafety and costs.

Where the host cell is a procaryote such as *E. coli*, competent cells which are capable of DNA uptake are prepared from cells harvested after exponential growth phase and subsequently treated by the CaCl$_2$ method by well known procedures. Transformation can also be performed after forming a protoplast of the host cell.

Where the host used is an eucaryote, transfection methods such as the use of a calcium phosphate-precipitate, electroporation, conventional mechanical procedures such as microinjection, insertion of a plasmid encapsulated in red blood cell ghosts or in liposomes, treatment of cells with agents such as lysophosphatidyl-choline or use of virus vectors, or the like may be used.

The level of production of a protein or polypeptide is governed by three major factors: (1) the number of copies of the gene or DNA sequence encoding for it within the cell; (2) the efficiency with which those gene and sequence copies are transcribed and translated; and (3) the stability of the mRNA. Efficiencies of transcription and translation (which together comprise expression) are in turn dependent upon nucleotide sequences, normally situated ahead of the desired coding sequence. Those nucleotide sequences or expression control sequences define, inter alia, the location at which an RNA polymerase interacts to initiate transcription (the promoter sequence) and at which ribosomes bind and interact with the mRNA (the product of transcription) to initiate translation. Not all such expression control sequences function with equal efficiency. It is thus of advantage to separate the specific coding sequences for the desired protein from their adjacent nucleotide sequences and fuse them instead to known expression control sequences so as to favor higher levels of expression. This having been achieved, the newly engineered DNA fragment may be inserted into a multicopy plasmid or a bacteriophage derivative in order to increase the number of gene or sequence copies within the cell and thereby further improve the yield of expressed protein.

Several expression control sequences may be employed. These include the operator, promoter and ribosome binding and interaction sequences (including sequences such as the Shine-Dalgarno sequences) of the lactose operon of E. coli ("the lac system"), the corresponding sequences of the tryptophan synthetase system of E. coli ("the trp system"), a fusion of the trp and lac promoter ("the tac system"), the major operator and promoter regions of phage lambda ($O_L P_L$ and $O_R P_{R'}$), and the control region of the phage fd coat protein. DNA fragments containing these sequences are excised by cleavage with restriction enzymes from the DNA isolated from transducing phages that carry the lac or trp operons, or from the DNA of phage lambda or fd. Those fragments are then manipulated in order to obtain a limited population of molecules such that the essential controlling sequences can be joined very close to, or in juxtaposition with, the initiation codon of the coding sequence.

The fusion product is then inserted into a cloning vehicle for transformation or transfection of the appropriate hosts and the level of antigen production is measured. Cells giving the most efficient expression may be thus selected. Alternatively, cloning vechicles carrying the lac, trp or lambda $P_L$ control system attached to an initiation codon may be employed-and fused to a fragment containing a sequence coding for a MN protein or polypeptide such that the gene or sequence is correctly translated from the initiation codon of the cloning vehicle.

The phrase "recombinant nucleic acid molecule" is herein defined to mean a hybrid nucleotide sequence comprising at least two nucleotide sequences, the first sequence not normally being found together in nature with the second.

The phrase "expression control sequence" is herein defined to mean a sequence of nucleotides that controls and regulates expression of structural genes when operatively linked to those genes.

Synthetic and Biologic Production of MN Proteins and Polypeptides

MN proteins and polypeptides of this invention may be prepared not only by recombinant means but also by synthetic and by other biologic means. Synthetic formation of the polypeptide or protein requires chemically synthesizing the desired chain of amino acids by methods well known in the art. Exemplary of other biologic means to prepare the desired polypeptide or protein is to subject to selective proteolysis a longer MN polypeptide or protein containing the desired amino acid sequence; for example, the longer polypeptide or protein can be split with chemical reagents or with enzymes.

Chemical synthesis of a peptide is conventional in the art and can be accomplished, for example, by the Merrifield solid phase synthesis technique [Merrifield, J., *Am. Chem. Soc.*, 85: 2149–2154 (1963); Kent et al., *Synthetic Peptides in Biology and Medicine*, 29 f.f. eds. Alitalo et al., (Elsevier Science Publishers 1985); and Haug, J. D., "Peptide Synthesis and Protecting Group Strategy", *American Biotechnology Laboratory*, 5(1): 40–47 (January/February 1987)].

Techniques of chemical peptide synthesis include using automatic peptide synthesizers employing commercially available protected amino acids, for example, Biosearch [San Rafael, Calif. (USA)] Models 9500 and 9600; Applied Biosystems, Inc. [Foster City, Calif. (USA)] Model 430; Milligen [a division of Millipore Corp.; Bedford, Mass. (USA)] Model 9050; and Du Pont's RAMP (Rapid Automated Multiple Peptide Synthesis) [Du Pont Compass, Wilmington, Del. (USA)].

Nucleic Acid Probes and Test Kits

Nucleic acid probes of this invention are those comprising sequences that are substantially complementary to the MN cDNA sequence shown in FIGS. 1A–1B or to MN gene sequences. The phrase "substantially complementary" is defined herein to have the meaning as it is well understood in the art and, thus, used in the context of standard hybridization conditions. The stringency of hybridization conditions can be adjusted to control the precision of complementarity.

Said probes can be used to detect MN DNA and/or RNA, and thus can be used to test for the presence or absence of MN genes, and amplification(s), mutation(s) or genetic rearrangements of MN genes in the cells of a patient. For example, overexpression of an MN gene may be detected by Northern blotting using probes of this invention. Gene alterations, as amplifications, translocations, inversions, and deletions among others, can be detected by using probes of this invention for in situ hybridization to chromosomes from a patient's cells, whether in metaphase spreads or interphase nuclei. Southern blotting could also be used with the probes of this invention to detect amplifications or deletions of MN genes. Restriction Fragment Length Polymorphism (RFLP) analysis using said probes is a preferred method of detecting gene alterations, mutations and deletions. Said probes can also be used to identify MN proteins and/or polypeptides as well as homologs or near homologs thereto by their hybridization to various RNAs transcribed from MN genes in different tissues.

Said probes thus can be useful diagnostically/ prognostically. Said probes can be embodied in test kits, preferably with appropriate means to enable said probes when hybridized to an appropriate MN gene or MN mRNA target to be visualized. Such samples include tissue specimens, body fluids and tissue and cell extracts.

Assays

Assays according to this invention are provided to detect and/or quantitate MN antigen or MN-specific antibodies in vertebrate samples, preferably mammalian samples, more preferably human samples. Such samples include tissue specimens, body fluids, tissue extracts and cell extracts. MN antigen may be detected by immunoassay, immunohistochemical staining, immunoelectron and scanning microscopy using immunogold among other techniques.

Preferred samples in which to assay MN antigen are tissue and/or cell extracts. (Examples 7 and 8 below are representative.) However, MN antigen may be detected in body fluids, which can include among other fluids: blood, serum, plasma, semen, breast exudate, saliva, tears, sputum, mucus, urine, lymph, cytosols, ascites, pleural effusions, amniotic fluid, bladder washes, bronchoalveolar lavages and cerebrospinal fluid. It is preferred that the MN antigen be concentrated from a larger volume of body fluid before testing. Preferred body fluids to assay would depend on the type of cancer for which one was testing, but in general preferred body fluids would be breast exudate, pleural effusions and ascites.

MN-specific antibodies can be bound by serologically active MN proteins/polypeptides in samples of such body fluids as blood, plasma, serum, lymph, mucus, tears, urine, spinal fluid and saliva; however, such antibodies are found most usually in blood, plasma and serum, preferably in serum. A representative assay to detect MN-specific antibodies is shown in Example 8 below wherein the fusion protein pGEX-3X-MN is used. Correlation of the results from the assays to detect and/or quantitate MN antigen and MN-specific antibodies reactive therewith, provides a preferred profile of the disease condition of a patient.

The assays of this invention are both diagnostic and/or prognostic, i.e., diagnostic/prognostic. The term "diagnostic/ prognostic" is herein defined to encompass the following processes either individually or cumulatively depending upon the clinical context: determining the presence of disease, determining the nature of a disease, distinguishing one disease from another, forecasting as to the probable outcome of a disease state, determining the prospect as to recovery from a disease as indicated by the nature and symptoms of a case, monitoring the disease status of a patient, monitoring a patient for recurrence of disease, and/or determining the preferred therapeutic regimen for a patient. The diagnostic/prognostic methods of this invention are useful, for example, for screening populations for the presence of neoplastic or pre-neoplastic disease, determining the risk of developing neoplastic disease, diagnosing the presence of neoplastic and/or pre-neoplastic disease, monitoring the disease status of patients with neoplastic disease, and/or determining the prognosis for the course of neoplastic disease.

The present invention is useful for screening for the presence of a wide variety of neoplastic diseases including carcinomas, such as, mammary, urinary tract, ovarian, uterine, cervical, endometrial, squamous cell and adenosquamous carcinomas; head and neck cancers; mesodermal tumors, such as, neuroblastomas and retinoblastomas; sarcomas, such as osteosarcomas and Ewing's sarcoma; and melanomas. Of particular interest are gynecological cancers including ovarian, uterine, cervical, vaginal, vulval and endometrial cancers, particularly ovarian, uterine cervical and endometrial cancers. Also of particular interest are cancers of the breast, of the stomach including esophagus, of the colon, of the kidney, of the prostate, of the liver, of the urinary tract including bladder, of the lung, and of the head and neck.

The invention provides methods and compositions for evaluating the probability of the presence of malignant or pre-malignant cells, for example, in a group of cells freshly removed from a host. Such an assay can be used to detect tumors, quantitate their growth, and help in the diagnosis and prognosis of disease. The assays can also be used to detect the presence of cancer metastasis, as well as confirm the absence or removal of all tumor tissue following surgery, cancer chemotherapy and/or radiation therapy. It can further be used to monitor cancer chemotherapy and tumor reappearance.

The presence of MN antigen or antibodies can be detected and/or quantitated using a number of well-defined diagnostic assays. Those in the art can adapt any of the conventional immunoassay formats to detect and/or quantitate MN antigen and/or antibodies. Example 8 details the format of a preferred diagnostic method of this invention—a radioimmunoassay. Many other formats for detection of MN antigen and MN-specific antibodies are, of course available. Those can be Western blots, ELISAs (enzyme-linked immunosorbent assays), RIAs (radioimmunoassay), competitive EIA or dual antibody sandwich assays, among other assays all commonly used in the diagnostic industry. In such immunoassays, the interpretation of the results is based on the assumption that the antibody or antibody combination will not cross-react with other proteins and protein fragments present in the sample that are unrelated to MN.

Representative of one type of ELISA test for MN antigen is a format wherein a microtiter plate is coated with antibodies made to MN proteins/polypeptides or antibodies made to whole cells expressing MN proteins, and to this is added a patient sample, for example, a tissue or cell extract. After a period of incubation permitting any antigen to bind to the antibodies, the plate is washed and another set of anti-MN antibodies which are linked to an enzyme is added, incubated to allow reaction to take place, and the plate is then rewashed. Thereafter, enzyme substrate is added to the microtiter plate and incubated for a period of time to allow the enzyme to work on the substrate, and the adsorbance of the final preparation is measured. A large change in absorbance indicates a positive result.

It is also apparent to one skilled in the art of immunoassays that MN proteins and/or polypeptides can be used to detect and/or quantitate the presence of MN antigen in the body fluids, tissues and/or cells of patients. In one such embodiment, a competition immunoassay is used, wherein the MN protein/polypeptide is labeled and a body fluid is added to compete the binding of the labeled MN protein/ polypeptide to antibodies specific to MN protein/ polypeptide. Such an assay can be used to detect and/or quantitate MN antigen as described in Example 8.

In another embodiment, an immunometric assay may be used wherein a labeled antibody made to a MN protein or polypeptide is used. In such an assay, the amount of labeled antibody which complexes with the antigen-bound antibody is directly proportional to the amount of MN antigen in the sample.

A representative assay to detect MN-specific antibodies is a competition assay in which labeled MN protein/ polypeptide is precipitated by antibodies in a sample, for example, in combination with monoclonal antibodies recognizing MN proteins/polypeptides. One skilled in the art could adapt any of the conventional immunoassay formats to detect and/or quantitate MN-specific antibodies. Detection of the binding of said antibodies to said MN protein/polypeptide could be by many ways known to those in the art, e.g., in humans with the use of anti-human labeled IgG.

An exemplary immunoassay method of this invention to detect and/or quantitate MN antigen in a vertebrate sample comprises the steps of:

a) incubating said vertebrate sample with one or more sets of antibodies (an antibody or antibodies) that bind to MN antigen wherein one set is labeled or otherwise detectable;

b) examining the incubated sample for the presence of immune complexes comprising MN antigen and said antibodies.

Another exemplary immunoassay method according to this invention is that wherein a competition immunoassay is used to detect and/or quantitate MN antigen in a vertebrate sample and wherein said method comprises the steps of:

a) incubating a vertebrate sample with one or more sets of MN-specific antibodies and a certain amount of a labeled or otherwise detectable MN protein/polypeptide wherein said MN protein/polypeptide competes for binding to said antibodies with MN antigen present in the sample;

b) examining the incubated sample to determine the amount of labeled/detectable MN protein/polypeptide bound to said antibodies; and c) determining from the results of the examination in step b) whether MN antigen is present in said sample and/or the amount of MN antigen present in said sample.

Once antibodies (including biologically active antibody fragments) having suitable specificity have been prepared, a wide variety of immunological assay methods are available for determining the formation of specific antibody-antigen complexes. Numerous competitive and non-competitive protein binding assays have been described in the scientific and patent literature, and a large number of such assays are commercially available. Exemplary immunoassays which are suitable for detecting a serum antigen include those described in U.S. Pat. Nos. 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876.

Antibodies employed in assays may be labeled or unlabeled. Unlabeled antibodies-may be employed in agglutination; labeled antibodies may be employed in a wide variety of assays, employing a wide variety of labels.

Suitable detection means include the use of labels such as radionuclides, enzymes, coenzymes, fluorescers, chemiluminescers, chromogens, enzyme substrates or co-factors, enzyme inhibitors, free radicals, particles, dyes and the like. Such labeled reagents may be used in a variety of well known assays, such as radioimmunoassays, enzyme immunoassays, e.g., ELISA, fluorescent immunoassays, and the like. See for example, U.S. Pat. Nos. 3,766,162; 3,791,932; 3,817,837; and 4,233,402.

Methods to prepare antibodies useful in the assays of the invention are described below. The examples below detail representative assays according to this invention.

Immunoassay Test Kits

The above outlined assays can be embodied in test kits to detect and/or quantitate MN antigen and/or MN-specific antibodies (including biologically active antibody fragments). Kits to detect and/or quantitate MN antigen can comprise MN protein(s)/polypeptides(s) and/or MN-specific antibodies, polyclonal and/or monoclonal. Such diagnostic/prognostic test kits can comprise one or more sets of antibodies, polyclonal and/or monoclonal, for a sandwich format wherein antibodies recognize epitopes on the MN antigen, and one set is appropriately labeled or is otherwise detectable.

Test kits for an assay format wherein there is competition between a labeled (or otherwise detectable) MN protein/polypeptide and MN antigen in the sample, for binding to an antibody, can comprise the combination of the labeled protein/polypeptide and the antibody in amounts which provide for optimum sensitivity and accuracy.

Test kits for MN-specific antibodies preferably comprise labeled/detectable MN proteins(s) and/or polypeptides(s), and may comprise other components as necessary, for example, to perform a preferred assay as outlined in Example 8 below. Such test kits can have other appropriate formats for conventional assays.

Preparation of MN-Specific Antibodies

The term "antibodies" is defined herein to include not only whole antibodies but also biologically active fragments of antibodies, preferably fragments containing the antigen binding regions. Such antibodies may be prepared by conventional methodology and/or by genetic engineering. Antibody fragments may be genetically engineered, preferably from the variable regions of the light and/or heavy chains ($V_H$ and $V_L$), including the hypervariable regions, and still more preferably from both the $V_H$ and $V_L$ regions. For example, the term "antibodies" as used herein comprehends polyclonal and monoclonal antibodies and biologically active fragments thereof including among other possibilities "univalent" antibodies [Glennie et al., Nature, 295: 712 (1982)]; Fab proteins including Fab' and F(ab')$_2$ fragments whether covalently or non-covalently aggregated; light or heavy chains alone, preferably variable heavy and light chain regions ($V_H$ and $V_L$ regions), and more preferably including the hypervariable regions [otherwise known as the complementarity determining regions (CDRs) of said $V_H$ and $V_L$ regions]; $F_c$ proteins; "hybrid" antibodies capable of binding more than one antigen; constant-variable region chimeras; "composite" immunoglobulins with heavy and light chains of different origins; "altered" antibodies with improved specificity and other characteristics as prepared by standard recombinant techniques and also by oligonucleotide-directed mutagenesis techniques [Dalbadie-McFarland et al., PNAS (USA), 79: 6409 (1982)].

It may be preferred for therapeutic and/or imaging uses that the antibodies be biologically active antibody fragments, preferably genetically engineered fragments, more preferably genetically engineered fragments from the $V_H$ and/or $V_L$ regions, and still more preferably comprising the hypervariable regions thereof.

There are conventional techniques for making polyclonal and monoclonal antibodies well-known in the immunoassay art. Immunogens to prepare MN-specific antibodies include MN proteins and/or polypeptides, preferably purified, and MX-infected tumor line cells, for example, MX-infected HeLa cells, among other immunogens.

Anti-peptide antibodies are also made by conventional methods in the art as described in European Patent Publication No. 44,710 (published Jan. 27, 1982). Briefly, such anti-peptide antibodies are prepared by selecting a peptide from an MN amino acid sequence as from FIG. 1, chemically synthesizing it, conjugating it to an appropriate immunogenic protein and injecting it into an appropriate animal, usually a rabbit or a mouse; then, either polyclonal or monoclonal antibodies are made, the latter by the Kohler-Milstein procedure.

Besides conventional hybridoma technology, newer technologies can be used to produce antibodies according to this invention. For example, the use of the polymerase chain reaction (PCR) to clone and express antibody V-genes and phage display technology to select antibody genes encoding fragments with binding activities has resulted in the isolation of antibody fragments from repertoires of PCR amplified V-genes using immunized mice or humans. [Marks et al., BioTechnology, 10: 779 (July 1992) for references; Chiang et al., BioTechniques, 7(4): 360 (1989); Ward et al., Nature, 341: 544 (Oct. 12, 1989); Marks et al., J. Mol. Biol., 222: 581 (1991); Clackson et al., Nature, 352: (Aug. 15, 1991); and Mullinax et al., PNAS (USA), 87: 8095 (October 1990).

Descriptions of preparing antibodies, which term is herein defined to include biologically active antibody fragments, by recombinant techniques can be found in U.S. Pat. No. 4,816,567 (issued Mar. 28, 1989); European Patent Application Publication Number (EP) 338,745 (published Oct. 25, 1989); EP 368,684 (published Jun. 16, 1990); EP 239,400 (published Sep. 30, 1987); WO 90/14424 (published Nov. 29, 1990); WO 90/14430 (published May 16, 1990); Huse et al., Science, 246: 1275 (Dec. 8, 1989); Marks et al., BioTechnology, 10: 779 (July 1992); La Sastry et al., PNAS (USA), 86: 5728 (August 1989); Chiang et al., BioTechniques, 7(40): 360 (1989); Orlandi et al., PNAS (USA), 86: 3833 (May 1989); Ward et al. Nature, 341: 544 (Oct. 12, 1989); Marks et al., J. Mol. Biol., 222: 581 (1991); and Hoogenboom et al., Nucleic Acids Res., 19(15): 4133 (1991).

Preparation of Monoclonal Antibodies

Monoclonal antibodies for use in the assays of this invention may be obtained by methods well known in the art for example, Galfre and Milstein, "Preparation of Monoclonal Antibodies: Strategies and Procedures," in Methods in Enzymology: Immunochemical Techniques. 73: 1–46 [Langone and Vanatis (eds); Academic Press (1981)]; and in the classic reference, Milstein and Kohler, Nature, 256: 495–497 (1975).

Although the representative hybridoma of this invention is formed by the fusion of murine cell lines, human/human hybridomas [Olsson et al., PNAS (USA), 77: 5429 (1980)] and human/murine hybridomas [Schlom et al., PNAS (USA), 77: 6841 (1980); Shearman et al. J. Immunol., 146: 928–935 (1991); and Gorman et al., PNAS (USA), 88: 4181–4185 (1991)] can also be prepared among other possibilities. Such humanized monoclonal antibodies would be preferred monoclonal antibodies for therapeutic and imaging uses.

Monoclonal antibodies specific for this invention can be prepared by immunizing appropriate mammals, preferably rodents, more preferably rabbits or mice, with an appropriate immunogen, for example, MaTu-infected HeLa cells or MN proteins/polypeptides attached to a carrier protein if necessary. The production of hybridoma VU-M75 which secretes MAb M75 is exemplary and described below. MAb M75 serves to identify MN proteins/polypeptides in various laboratory diagnostic tests, for example, in tumor cell cultures or in clinical samples. Also produced by the method described for producing MAb M75 (isotype IgG2B) were MAbs M16 (isotype IgG2A) and M67 (isotype IgG1).

MAb M75

Monoclonal antibody M75 (MAb M75) is produced by mouse lymphocytic hybridoma VU-M75, which was initially deposited in the Collection of Hybridomas at the Institute of Virology, Slovak Academy of Sciences (Bratislava, Czechoslovakia) and was deposited under ATCC Designation HB 11128 on Sep. 17, 1992 at the American Type Culture Collection (ATCC) in Manassas, Va. (USA).

Hybridoma VU-M75 was produced according to the procedure described in Gerhard, W., "Fusion of cells in suspension and outgrowth of hybrids in conditioned medium," In: Monoclonal Antibodies. Hybridomas: A New Dimension in Biological Analysis, page 370 [Kennet et al. (eds.); Plenum N.Y. (USA)]. BALB/C mice were immunized with MaTu-infected HeLa cells, and their spleen cells were fused with myeloma cell line NS-0. Tissue culture media from the hybridomas were screened for monoclonal antibodies, using as antigen the p58 immunoprecipitated from cell extracts of MaTu-infected HeLa with rabbit anti-MaTu serum and protein A-Staphylococcus aureus cells (SAC) [Zavada and Zavadova, Arch. Virol., 118 189–197 (1991)], and eluted from SDS-PAGE gels. Monoclonal antibodies were purified from TC media by affinity chromatography on protein A-Sepharose [Harlow and Lane, "Antibodies: A Laboratory Manual," Cold Spring Harbor, Cold Spring Harbor, N.Y. (USA); 1988].

The monoclonal antibodies useful according to this invention to identify MN proteins/polypeptides can be labeled in any conventional manner, for example, with enzymes such as horseradish peroxidase (HRP), fluorescent compounds, or with radioactive isotopes such as, $^{125}I$, among other labels. A preferred label, according to this invention is $^{125}I$, and a preferred method of labeling the antibodies is by using chloramine-T [Hunter, W. M., "Radioimmunoassay," In: Handbook of Experimental Immunology, pp. 14.1–14.40 (D. W. Weir ed.; Blackwell, Oxford/London/Edinburgh/Melbourne; 1978)].

MAb H460

Monoclonal antibody H460 (MAb H460) was prepared in a manner similar to that for MAb M75 except that the mice were immunized with HeLa cells uninfected with MaTu, and lymphocytes of the mice rather than spleen cells were fused with cells from myeloma cell line NS-0. MAb H460 reacts about equally with any human cells.

Therapeutic Use of MN-Specific Antibodies

The MN-specific antibodies of this invention, monoclonal and/or polyclonal, preferably monoclonal, more preferably MAb M75, may be used therapeutically in the treatment of neoplastic and/or pre-neoplastic disease, either alone or in combination with chemotherapeutic drugs or toxic agents, such as ricin A. Further preferred for therapeutic use would be biologically active antibody fragments as described herein. Also preferred MN-specific antibodies for such therapeutic uses would be humanized monoclonal antibodies.

The MN-specific antibodies can be administered in a therapeutically effective amount, preferably dispersed in a physiologically acceptable, nontoxic liquid vehicle.

Imaging Use of Antibodies

Further, the MN-specific antibodies of this invention when linked to an imaging agent, such as a radionuclide, can be used for imaging. Biologically active antibody fragments or humanized monoclonal antibodies, may be preferred for imaging use.

A patient's neoplastic tissue can be identified as, for example, sites of tumors and locations of any metastases. Antibodies, appropriately labeled or linked to an imaging agent, can be injected in a physiologically acceptable carrier into a patient, and the binding of the antibodies can be detected by a method appropriate to the label or imaging agent, for example, by scintigraphy.

Antisense MN Nucleic Acid Sequences

MN genes are herein considered putative oncogenes and the proteins encoded thereby are considered to be putative oncoproteins. Antisense nucleic acid sequences substantially complementary to mRNA transcribed from MN genes, as represented by the antisense oligodeoxynucleotides (ODNS) of Example 11, infra, can be used to reduce or prevent expression of the MN gene. [Zamecnick, P. C., "Introduction: Oligonucleotide Base Hybridization as a Modulator of Genetic Message Readout," pp. 1–6, *Prospects for Antisense Nucleic Acid Therapy of Cancer and AIDS,* (Wiley-Liss, Inc., New York, N.Y., USA; 1991); Wickstrom, E., "Antisense DNA Treatment of HL-60 Promyelocytic Leukemia Cells: Terminal Differentiation and Dependence on Target Sequence," pp. 7–24, id.; Leserman et al., "Targeting and Intracellular Delivery of Antisense Oligonucleotides Interfering with oncogene Expression," pp. 25–34, id.; Yokoyama, K., "Transcriptional Regulation of c-myc Protooncogene by Antisense RNA," pp. 35–52, id.; van den Berg et al., "Antisense fos Oligodeoxyribonucleotides Suppress the Generation of Chromosomal Aberrations," pp. 63–70, id.; Mercola, D., "Antisense fos and fun RNA," pp. 83–114, id.; Inouye, *Gene,* 72: 25–34 (1988); Miller and Ts'o, *Ann. Reports Med. Chem.,* 23: 295–304 (1988); Stein and Cohen, *Cancer Res.,* 48: 2659–2668 (1988); Stevenson and Inversen, *J. Gen. Virol.,* 70: 2673–2682 (1989); Goodchild, "Inhibition of Gene Expression by Oligonucleotides," pp. 53–77, *Oligodeoxynucleotides: Antisense Inhibitors of Gene Expression* (Cohen, J. S., ed; CRC Press, Boca Raton, Fla., USA; 1989); Dervan et al., "Oligonucleotide Recognition of Double-helical DNA by Triple-helix Formation," pp. 197–210, id.; Neckers, L. M., "Antisense Oligodeoxynucleotides as a Tool for Studying Cell Regulation: Mechanisms of Uptake and Application to the Study of oncogene Function," pp. 211–232, id.; Leitner et al., *PNAS* (USA), 87: 3430–3434 (1990); Bevilacqua et al., *PNAS* (USA), 85: 831–835 (1988); Loke et al. *Curr. Top. Microbiol. Immunol.,* 141: 282–288 (1988); Sarin et al., *PNAS* (USA), 85: 7448–7451 (1988); Agrawal et al., "Antisense Oligonucleotides: A Possible Approach for Chemotherapy and AIDS," International Union of Biochemistry Conference on Nucleic Acid Therapeutics (Jan. 13–17, 1991; Clearwater Beach, Fla., USA); Armstrong, L., *Ber. Week,* pp. 88–89 (Mar. 5, 1990); and Weintraub et al., *Trends,* 1: 22–25 (1985).] Such antisense nucleic acid sequences, preferably oligonucleotides, by hybridizing to the MN mRNA, particularly in the vicinity of the ribosome binding site and translation initiation point, inhibits translation of the mRNA. Thus, the use of such antisense nucleic acid sequences may be considered to be a form of cancer therapy.

Preferred antisense oligonucleotides according to this invention are gene-specific ODNs or oligonucleotides complementary to the 5' end of MN mRNA. Particularly preferred are the 29-mer ODN1 and 19-mer ODN2 for which the sequences are provided in Example 11, infra. Those antisense ODNs are representative of the many antisense nucleic acid sequences that can function to inhibit MN gene expression. Ones of ordinary skill in the art could determine appropriate antisense nucleic acid sequences, preferably antisense oligonucleotides, from the nucleic acid sequence of FIGS. 1A–1B.

Vaccines

It will be readily appreciated that MN proteins and polypeptides of this invention can be incorporated into vaccines capable of inducing protective immunity against neoplastic disease and a dampening effect upon tumorigenic activity. MN proteins and/or polypeptides may be synthesized or prepared recombinantly or otherwise biologically, to comprise one or more amino acid sequences corresponding to one or more epitopes of the MN proteins either in monomeric or multimeric form. Those proteins and/or polypeptides may then be incorporated into vaccines capable of inducing protective immunity. Techniques for enhancing the antigenicity of such polypeptides include incorporation into a multimeric structure, binding to a highly immunogenic protein carrier, for example, keyhole limpet hemocyanin (KLH), or diptheria toxoid, and administration in combination with adjuvants or any other enhancers of immune response.

Preferred MN proteins/polypeptides to be used in a vaccine according to this invention would be genetically engineered MN proteins. A preferred recombinant MN protein is the fusion protein pGEX-3X-MN, produced according to this invention.

A preferred exemplary use of such a vaccine of this invention would be its administration to patients whose MN-carrying primary cancer had been surgically removed. The vaccine may induce active immunity in the patients and prevent recidivism or metastasis.

It will further be appreciated that anti-idiotype antibodies to antibodies to MN proteins/polypeptides are also useful as vaccines and can be similarly formulated.

An amino acid sequence corresponding to an epitope of an MN protein/polypeptide either in monomeric or multimeric form may also be obtained by chemical synthetic means or by purification from biological sources including genetically modified microorganisms or their culture media [See Lerner, "Synthetic Vaccines", *Sci. Am.* 248(2): 66–74 (1983)]. The protein/polypeptide may be combined in an amino acid sequence with other proteins/polypeptides including fragments of other proteins, as for example, when synthesized as a fusion protein, or linked to other antigenic or non-antigeneic polypeptides of synthetic or biological origin.

The term "corresponding to an epitope of an MN protein/polypeptide" will be understood to include the practical possibility that, in some instances, amino acid sequence variations of a naturally occurring protein or polypeptide may be antigenic and confer protective immunity against neoplastic disease and/or anti-tumorigenic effects. Possible sequence variations include, without limitation, amino acid substitutions, extensions, deletions, truncations, interpolations and combinations thereof. Such variations fall within the contemplated scope of the invention provided the protein or polypeptide containing them is immunogenic and antibodies elicited by such a polypeptide or protein cross-react with naturally occurring MN proteins and polypeptides to a sufficient extent to provide protective immunity and/or anti-tumorigenic activity when administered as a vaccine.

Such vaccine compositions will be combined with a physiologically acceptable medium, including immunologically acceptable diluents and carriers as well as commonly employed adjuvants such as Freund's Complete Adjuvant, saponin, alum, and the like. Administration would be in immunologically effective amounts of the MN proteins or polypeptides, preferably in quantities providing unit doses of from 0.01 to 10.0 micrograms of immunologically active MN protein and/or polypeptide per kilogram of the recipient's body weight. Total protective doses may range from 0.1 to about 100 micrograms of antigen.

Routes of administration, antigen dose, number and frequency of injections are all matters of optimization within the scope of the ordinary skill in the art.

The following examples are for purposes of illustration only and not meant to limit the invention in any way.

Materials and Methods

The following materials and methods were used in the Examples below.

MaTu-Infected and Uninfected HeLa Cells

MaTu agent [Zavada et al., Nature New Biol., 240: 124–125 (1972); Zavada et al., J. Gen. Virol. 24: 327–337 (1974)] was from original "MaTu" cells [Widmaier et al., Arch. Geschwulstforsch, 44: 1–10 (1974)] transferred into our stock of HeLa by cocultivation with MaTu cells treated with mitomycin C, to ensure that control and MaTu-infected cells were comparable. MaTu cells were incubated for 3 hours at 37° C. in media with 5 µg/ml of mitomycin C [Calbiochem, LaJolla, Calif. (USA)]. Mixed cultures were set to $2\times10^5$ of mitomycin C-treated cells and $4\times10^5$ of fresh recipient cells in 5 ml of medium. After 3 days they were first subcultured and further passaged 1–2 times weekly.

Control HeLa cells were the same as those described in Zavada et al., Nature New Biol., 240: 124–125 (1972).

Sera

Human sera from cancer patients, from patients suffering with various non-tumor complaints and from healthy women were obtained from the Clinics of Obstetrics and Gynaecology at the Postgraduate Medical School, Bratislava, Czechoslovakia.

Human sera KH was from a fifty year old mammary carcinoma patient, fourteen months after resection. That serum was one of two sera out of 401 serum samples that contained neutralizing antibodies to the VSV(MaTU) pseudotype as described in Zavada et al., Nature New Biology, 240: 124–125 (1972). Serum L8 was from a patient with Paget's disease. Serum M7 was from a healthy donor.

Rabbit anti-MaTu serum was prepared by immunizing a rabbit three times at intervals of 30 days with $10-5\times10^7$ viable MaTu infected HeLa cells.

RIP and PAGE

RIP and PAGE were performed essentially as described in Zavada and Zavadova, Arch. Virol., 118: 189– 197 (1991), except that in the experiments described herein [$^{35}$S] methionine (NEN), 10 µCi/ml of methionine-free MEM medium, supplemented with 2% FCS and 3% complete MEM were used. Confluent petri dish cultures of cells were incubated overnight in that media.

For RIP, the SAC procedure [Kessler, J. Immunol., 115: 1617–1624 (1975)] was used. All incubations and centrifugations were performed at 0–4° C. Cell monolayers were extracted with RIPA buffer (0.14 M NaCl, 7.5 mM phosphate buffer, pH 7.2, 1% Triton X-100, 0.1% sodium deoxycholate, 1 mM phenylmethylsulfonyl fluoride and Trasylol). To reduce non-specific reactions, antisera were preabsorbed with foetal calf serum [Barbacid et al., PNAS (USA), 77: 1617–1621 (1980)] and antigenic extracts with SAC.

For PAGE (under reducing conditions) we used 10% gels with SDS [Laemmli, Nature, 227: 680–685 (1970)]. As reference marker proteins served the Sigma kit (product MW-SDS-200). For fluorography we used salicylate [Heegaard et al., Electrophoresis, 5: 263–269 (1984)].

Immunoblots

Immunoblotting used as described herein follows the method of Towbin et al., PNAS (USA), 76: 4350–4354 (1979). The proteins were transferred from the gels onto nitrocellulose [Schleicher and Schuell; Dassel Germany; 0.45 µm porosity] in Laemmli electrode buffer diluted 1:10 with distilled water, with no methanol or SDS. The transfer was for 2½ hours at 1.75 mA/cm². The blots were developed with $^{125}$I-labeled MAbs and autoradiography was performed using intensifying screens, with X-ray films exposed at –70° C.

In extracts from cell cultures containing only small amounts of MN antigen, we concentrated the antigen from 0.5 or 1 ml of an extract by adding 50 µl of a 10% SAC suspension, pre-loaded with MAb M75. This method allowed the concentration of MN antigen even from clinical specimens, containing human IgG; preliminary control experiments showed that such a method did not interfere with the binding of the MN antigen to SAC-adsorbed M75. Tissue extracts were made by grinding the tissue with a mortar and pestle and sand (analytical grade). To the homogenates was added RIPA buffer, 10:1 (volume to weight) of original tissue. The extracts were clarified for 3 minutes on an Eppendorf centrifuge.

Example 1

Immunofluorescence of MaTu-Specific Antigens

Immunofluorescence experiments were performed on control and MaTu-infected HeLa cells with monoclonal antibodies, prepared as described above, which are specific for MaTu-related antigens. FITC-conjugated anti-mouse IgG was used to detect the presence of the monoclonal antibodies. Staining of the cells with Giemsa revealed no clear differences between control and MaTu-infected HeLa cells.

MAbs, which in preliminary tests proved to be specific for MaTu-related antigens, showed two different reactivities in immunofluorescence. A representative of the first group, MAb M67, gave a granular cytoplasmic fluorescence in MaTu-infected HeLa, which was only seen in cells fixed with acetone; living cells showed no fluorescence. MAb M16 gave the same type of fluorescence. With either M67 or M16, only extremely weak "background" fluorescence was seen in control HeLa cells.

Another MAb, M75, showed a granular membrane fluorescence on living MaTu-infected cells and a granular nuclear fluorescence in acetone-fixed cells. However, M75 sometimes showed a similar, although much weaker, fluorescence on uninfected HeLa cells. A relationship was observed based upon the conditions of growth: in HeLa cells uninfected with MaTu, both types of fluorescence with MAb M75 were observed only if the cells were grown for several passages in dense cultures, but not in sparse ones.

The amount of M75-reactive cell surface antigen was analyzed cytofluorometrically and was dependent on the density of the cell cultures and on infection with MaTu. Control and MaTu infected HeLa cells were grown for 12 days in dense or sparse cultures. The cells were released with Versene (EDTA), and incubated with MAb M75 or with no MAb, and subsequently incubated with FITC-conjugated anti-mouse IgG. The intensity of fluorescence was measured.

It appeared that the antigen binding MAb M75 is inducible: it was found to be absent in control HeLa grown in sparse culture, and to be induced either by the growth of HeLa in dense culture or by infection with MaTu. Those two factors were found to have an additive or synergistic effect. Those observations indicated along with other results described herein that there were two different agents involved: exogenous, transmissible MX, reactive with M67, and endogenous, inducible MN, detected by MAb M75.

Example 2

Immunoblot Analysis of Protein(s) Reactive with MAb M75

To determine whether MAb M75 reacts with the same protein in both uninfected and MaTu-infected HeLa, and to determine the molecular weight of the protein, extracts of those cells were analyzed by PAGE and immunoblotting (as described above). HeLa cells uninfected or MaTu-infected, that had been grown for 12 days in dense or sparse cultures, were seeded in 5-cm petri dishes, all variants at $5\times10^5$ cells per dish. Two days later, the cells were extracted with RIPA buffer (above described), 200 µl dish. The extracts were mixed with 2× concentrated Laemmli sample buffer containing 6% mercaptoethanol and boiled for five minutes. Proteins were separated by SDS-PAGE and blotted on nitrocellulose. The blots were developed with $^{125}$I-labeled MAb M75 and autoradiography.

MAb M75 reacted with two MN-specific protein bands of 54 kd and 58 kd, which were the same in uninfected HeLa grown at high density and in MaTu-infected HeLa, evidencing that M75 recognizes the same protein(s) in both uninfected and MaTu-infected HeLa cells. Consistent with the cytofluorometric results, the amount of the antigen depended both on cell density and on infection with MaTu, the latter being a much more potent inducer of p54/58N.

Example 3

Radioimmunoassay of MaTu-Specific Antigens In Situ

In contrast to the results with M75, the other MAb, M67, appeared to be specific for the exogenous, transmissible agent MX. With M67 we observed no immunofluorescence in control HeLa, regardless of whether the cells were grown in dense or in sparse culture. That difference was clearly evidenced in radioimmunoassay experiments wherein $^{125}$I-labeled MAbs M67 and M75 were used.

For such experiments, parallel cultures of uninfected and MaTu-infected cells were grown in dense or sparse cultures. The cultures were either live (without fixation), or fixed (with methanol for five minutes and air-dried). The cultures were incubated for two hours in petri dishes with the $^{125}$I-labeled MAbs, $6\times10^4$ cpm/dish. Afterward, the cultures were rinsed four times with PBS and solubilized with 1 ml/dish of 2 N NaOH, and the radioactivity was determined on a gamma counter.

The simple radioimmunoassay procedure of this example was performed directly in petri dish cultures. Sixteen variants of the radioimmunoassay enabled us to determine whether the MX and MN antigens are located on the surface or in the interior of the cells and how the expression of those two antigens depends on infection with MaTu and on the density, in which the cells had been grown before the petri dishes were seeded. In live, unfixed cells only cell surface antigens can bind the MAbs. In those cells, M67 showed no reaction with any variant of the cultures, whereas M75 reacted in accord with the results of Examples 1 and 2 above.

Fixation of the cells with methanol made the cell membrane permeable to the MAbs: M67 reacted with HeLa infected with MaTu, independently of previous cell density, and it did not bind to control HeLa. MAb M75 in methanol-fixed cells confirmed the absence of corresponding antigen in uninfected HeLa from sparse cultures and its induction both by growth in dense cultures and by infection with MaTu.

Example 4

Identification of MaTu Components Reactive with Animal Sera or Associated with VSV Virions Immunoblot analyses of MaTu-specific proteins from RIPA extracts from uninfected or MaTu-infected HeLa and from purified VSV reproduced in control or in MaTu-infected HeLa, identified which of the antigens, p58X or p54/58N, were radioimmunoprecipitated with animal sera, and which of them was responsible for complementation of VSV mutants and for the formation of pseudotype virions. Details concerning the procedures can be found in Pastorekova et al., *Virology*, 187: 620–626 (1992).

The serum of a rabbit immunized with MaTu-infected HeLa immunoprecipitated both MAb M67- and MAb M75-reactive proteins (both p58X and p54/58N), whereas the "spontaneously" immune sera of normal rabbit, sheep or leukemic cow immunoprecipitated only the M67-reactive protein (p58X). On the other hand, in VSV reproduced in MaTu-infected HeLa cells and subsequently purified, only the M75-reactive bands of p54/58N were present. Thus, it was concluded that MX and MN are independent components of MaTu, and that it was p54/58N that complemented VSV mutants and was assembled into pseudotype virions.

As shown in FIG. 6 discussed below in Example 5, MX antigen was found to be present in MaTu-infected fibroblasts. In Zavada and Zavadova (1991), it was reported that a p58 band from MX-infected fibroblasts could not be detected by RIP with rabbit anti-MaTu serum. That serum contains more antibodies to MX than to MN antigen. The discrepancy can be explained by the extremely slow spread of MX in infected cultures. The results reported in Zavada and Zavadova (1991) were from fibroblasts tested 6 weeks after infection, whereas the later testing was 4 months after infection. We have found by immunoblots that MX can be first detected in both H/F-N and H/F-T hybrids after 4 weeks, in HeLa cells after six weeks and in fibroblasts only 10 weeks after infection.

Example 5

Expression of MN- and MX-Specific Proteins

FIG. 6 graphically illustrates the expression of MN- and MX- specific proteins in human fibroblasts, in HeLa cells and in H/F-N and H/F-T hybrid cells, and contrasts the expression in MX-infected and uninfected cells. Cells were infected with MX by co-cultivation with mitomycin C-treated MX-infected HeLa. The infected and uninfected cells were grown for three passages in dense cultures. About four months after infection, the infected cells concurrently with uninfected cells were grown in petri dishes to produce dense monolayers.

A radimmunoassay was performed directly in confluent petri dish (5 cm) culture of cells, fixed with methanol essentially as described in Example 3, supra. The monolayers were fixed with methanol and treated with $^{125}$I-labeled MAbs M67 (specific for exogenous MX antigen) or M75 (specific for endogenous MN antigen) at $6 \times 10^4$ cpm/dish. The bound radioactivity was measured; the results are shown in FIG. 6.

FIG. 6 shows that MX-was transmitted to all four cell lines tested, that is, to human embryo fibroblasts, to HeLa and to both H/F-N and H/F-T hybrids; at the same time, all four uninfected counterpart cell lines were MX-negative (top graph of FIG. 6). MN antigens are shown to be present in both MX-infected and uninfected HeLa and H/F-T cells, but not in the fibroblasts (bottom graph of FIG. 6). No MN antigen was found in the control H/F-N, and only a minimum increase over background of MN antigen was found in MaTu infected H/F-N. Thus, it was found that in the hybrids, expression of MN antigen very strongly correlates with tumorigenicity.

Those results were consistent with the results obtained by immunoblotting as shown in FIG. 7. The MN-specific twin protein p54/58N was detected in HeLa cell lines (both our standard type, that is, HeLa K, and in the Stanbridge mutant HeLa, that is, D98/AH.2 shown as HeLa S) and in tumorigenic H/F-T; however, p54/58N was not detected in the fibroblasts nor in the non-tumorigenic H/F-N even upon deliberately long exposure of the film used to detect radioactivity. Infection of the HeLa cells with MX resulted in a strong increase in the concentration of the p54/58N protein (s).

The hybrid cells H/F-N and H/F-T were constructed by Eric J. Stanbridge [Stanbridge et al., *Somatic Cell Genetics.* 7: 699–712 (1981); and Stanbridge et al., *Science,* 215: 252–259 (1982)]. His original hybrid, produced by the fusion of a HeLa cell and a human fibroblast was not tumorigenic in nude mice, although it retained some properties of transformed cells, for example, its growth on soft agar. Rare segregants from the hybrid which have lost chromosome 11 are tumorigenic. The most likely explanation for the tumorigenicity of those segregants is that chromosome 11 contains a suppressor gene (an antioncogene), which blocks the expression of a as yet unknown oncogene. The oncoprotein encoded by that oncogene is critical for the capacity of the H/F hybrids to produce tumors in nude mice. Since the p54/58N protein shows a correlation with the tumorigenicity of H/F hybrids, it is a candidate for that putative oncoprotein.

Example 6

Immunoblots of MN Antigen from Human Tumor Cell Cultures and from Clinical Specimens of Human Tissues The association of MN antigen with tumorigenicity in the H/F hybrid cells as illustrated by Example 5 prompted testing for the presence of MN antigen in other human tumor cell cultures and in clinical specimens. Preliminary experiments indicated that the concentration of MN antigen in the extracts from other human tumor cell cultures was lower than in HeLa; thus, it was realized that long exposure of the autoradiographs would be required. Therefore, the sensitivity of the method was increased by the method indicated under *Materials and Methods: Immunoblotting,* supra, wherein the MN antigen was concentrated by precipitation with MAb M75-loaded SAC.

FIG. 8 shows the immunoblots wherein lane A, a cell culture extract from MX-infected HeLa cells was analysed directly (10 μl per lane) whereas the antigens from the other extracts (lanes B–E) were each concentrated from a 500 μl extract by precipitation with MAb M75 and SAC.

FIG. 8 indicates that two other human carcinoma cell lines contain MN-related proteins—T24 (bladder carcinoma; lane C) and T47D (mammary carcinoma; lane D). Those cells contain proteins which react with MAb M75 that under reducing conditions have molecular weights of 54 kd and 56 kd, and under non-reducing conditions have a molecular weight of about 153 kd. The intensity of those bands is at least ten times lower than that for the p54/58N twin protein from HeLa cells.

An extremely weak band at approximately 52 kd could be seen under reducing conditions from extracts from human melanoma cells (SK-Mel 1477;lane E), but no bands for human fibroblast extracts (lane B) could be seen either on the reducing or non-reducing gels.

FIG. 9 shows immunoblots of human tissue extracts including surgical specimens as compared to a cell extract from MX-infected HeLa (lane A). The MN-related antigen from all the extracts but for lane A (analysed directly at 10 μl per lane) was first concentrated from a 1 ml extract as explained above. MN proteins were found in endometrial (lanes D and M), ovarian (lanes E and N) and in uterine cervical (lane 0) carcinomas. In those extracts MN-related proteins were found in three bands having molecular weights between about 48 kd and about 58 kd. Another MN-related protein was present in the tissue extract from a mammary papilloma; that protein was seen as a single band at about 48 kd (lane J).

Clearly negative were the extracts from full-term placenta (lane B), normal mammary gland (lane K), hyperplastic endometrium (lane L), normal ovaries (lane H), and from uterine myoma (lane I). Only extremely slightly MN-related bands were seen in extracts from trophoblasts (lanes F and G) and from melanoma (lane P).

The observations that antigen related to p54/58N was expressed in clinical specimens of several types of human carcinomas but not in normal tissues of corresponding organs further strengthens the association of MN antigen with tumorigenesis. However, it should be noted that for human tumors, a normal tissue is never really an adequate control in that tumors are believed not to arise from mature, differentiated cells, but rather from some stem cells, capable of division and of differentiation. In body organs, such cells may be quite rare.

Example 7

MN Antigen in Animal Cell Lines

Since the MN gene is present in the chromosomal DNA of all vertebrate species that were tested, MN-related antigen was searched for also in cell lines derived from normal tissues and from tumors of several animal species. MN-related protein was found in two rat cell lines: one of them was the XC cell line derived from rat rhabdomyosarcoma induced with Rous sarcoma virus; the other was the Rat2-Tk⁻ cell line. In extracts from both of those rat cell lines, a single protein band was found on the blots: its molecular weight on blots produced from a reducing gel and from a non-reducing gel was respectively 53.5 kd and 153 kd. FIG. 10 shows the results with Rat2-Tk⁻ cell extracts (lane B), compared with extracts from MX-infected HeLa (lane A); the concentration of MN antigen in those two cell lines is very similar. The extracts were analysed directly (40 µl per lane).

MN-related protein from XC cells showed the same pattern as for Rat2-Tk⁻ cells both under reducing and non-reducing conditions, except that its concentration was about 30× lower. The finding of a MN-related protein—p53.5N—in two rat cell lines (FIGS. 10 and 12) provides the basis for a model system.

None of the other animal cell lines tested contained detectable amounts of MN antigen, even when the highly sensitive immunoblot technique in which the MN antigens are concentrated was used. The MN-negative cells were: Vero cells (African green monkey); mouse L cells; mouse NIH-3T3 cells normal, infected with Moloney leukemia virus, or transformed with Harvey sarcoma virus; GR cells (mouse mammary tumor cells induced with MTV), and NMG cells (normal mouse mammary gland).

Example 8

Radioimmunoassays in Liquid Phase Using Recombinant MN Protein for MN-Specific Antibodies and for MN Antigen The genetically engineered MN protein fused with glutathione S-transferase—pGEX-3X-MN—prepared and purified as described above was labeled with $^{125}$I by the chloramine T method [Hunter (1978)]. The purified protein enabled the development of a quantitative RIA for MN-specific antibodies as well as for MN antigens. All dilutions of antibodies and of antigens were prepared in RIPA buffer (1% TRITON X-100 and 0.1% sodium deoxycholate in PBS—phosphate buffered saline, pH 7.2), to which was added 1% of foetal calf serum (FCS). Tissue and cell extracts were prepared in RIPA buffer containing 1 mM phenylmethylsulfonylfluoride and 200 trypsin inhibiting units of Trasylol (aprotinin) per ml, with no FCS. $^{125}$I-labeled pGEX-3X-MN protein (2.27 µCi/µg of TCA-precipitable protein) was before use diluted with RIPA+1% FCS, and non-specifically binding radioactivity was adsorbed with a suspension of fixed protein A-*Staphylococcus aureus* cells (SAC).

In an RIA for MU-specific antibodies, MAb-containing ascites fluids or test sera were mixed with $^{125}$I-labeled protein and allowed to react in a total volume of 1 ml for 2 hours at room temperature. Subsequently, 50 µl of a 10% suspension of SAC [Kessler, supra] was added and the mixture was incubated for 30 minutes. Finally, the SAC was pelleted, 3× washed with RIPA, and the bound radioactivity was determined on a gamma counter.

Titration of antibodies to MN antigen is shown in FIG. 11. Ascitic fluid from a mouse carrying M75 hybridoma cells (A) is shown to have a 50% end-point at dilution $1:1.4\times10^{-6}$. At the same time, ascitic fluids with MAbs specific for MX protein (M16 and M67) showed no precipitation of $^{125}$I-labeled pGEX-3X-MN even at dilution 1:200 (result not shown). Normal rabbit serum (C) did not significantly precipitate the MN antigen; rabbit anti-MaTu serum (B), obtained after immunization with live MX-infected HeLa cells, precipitated 7% of radioactive MN protein, when diluted 1:200. The rabbit anti-MaTu serum is shown by immunoblot in Example 4 (above) to precipitate both MX and MN proteins.

Only one out of 180 human sera tested (90 control and 90 sera of patients with breast, ovarian or uterine cervical cancer) showed a significant precipitation of the radioactively labeled MN recombinant protein. That serum—L8—(D) was retested on immunoblot (as in Example 4), but it did not precipitate any p54/58N from MX-infected HeLa cells. Also, six other human sera, including KH (E), were negative on immunoblot. Thus, the only positive human serum in the RIA, L8, was reactive only with the genetically engineered product, but not with native p54/58N expressed by HeLa cells.

In an RIA for MN antigen, the dilution of MAb M75, which in the previous test precipitated 50% of maximum precipitable radioactivity (=dilution $1:1.4\times10^{-6}$) was mixed with dilutions of cell extracts and allowed to react for 2 hours. Then, $^{125}$I-labeled pGEX-3X-MN ($25\times10^3$ cpm/tube) was added for another 2 hours. Finally, the radioactivity bound to MAb M75 was precipitated with SAC and washed as above. One hundred percent precipitation (=0 inhibition) was considered the maximum radioactivity bound by the dilution of MAb used. The concentration of the MN antigen in the tested cell extracts was calculated from an inhibition curve obtained with "cold" pGEX-3X-MN, used as the standard (A in FIG. 12).

The reaction of radioactively labeled pGEX-3X-MN protein with MAb M75 enabled us to quantitate MN antigen directly in cell extracts. FIG. 12 shows that 3 ng of "cold" pGEX-3X-MN(A) caused a 50% inhibition of precipitation of "hot" pGEX-3X-MN; an equivalent amount of MN antigen is present in $3\times10^3$ ng of proteins extracted from MaTu-infected HeLa (B) or from Rat2-Tk⁻ cells (C). Concentrations of MN protein in cell extracts, determined by this RIA, are presented in Table 1 below. It must be understood that the calculated values are not absolute, since MN antigens in cell extracts are of somewhat different sizes, and also since the genetically engineered MN protein is a product containing molecules of varying size.

TABLE 1

Concentration of MN Protein in Cell Extracts

| Cells | ng MN/mg total protein |
|---|---|
| HeLa + MX | 939.00 |
| Rat2-Tk⁻ | 1065.00 |
| HeLa | 27.50 |
| XC | 16.40 |
| T24 | 1.18 |
| HEF | 0.00 |

The data were calculated from the results shown in FIG. 12.

Example 9

RIP of MX Antigen

An approximate concentration of p58X protein can be obtained by RIP from extracts of MaTu-infected HeLa cells that have been metabolically labeled with [$^{35}$S]-methionine or with a mixture of [$^{14}$C]-amino acids. The results are shown in Table 2.

TABLE 2

Radioimmunoprecipitation of metabolically labeled p58X protein

| Label | Interval | Cells | Total cpm × 10⁻⁶ | Precipit. with MAb M16 + SAC cpm × 10⁻³ | | % cpm in p58X |
|---|---|---|---|---|---|---|
| | | | | Prec. 1 | Prec. 2 | (prec. 1 + 2) |
| ³⁵S methionine | A | HeLa | 7.850 | 11.455 | 7.631 | 0 |
| | | HeLa + MX | 9.337 | 93.797 | 12.117 | 0.891 |
| | B | HeLa | 6.270 | 7.299 | 5.947 | 0 |
| | | HeLa + MX | 6.469 | 67.099 | 7.346 | 0.935 |
| ¹⁴C amino acids | A | HeLa | 4.223 | 6.423 | 4.168 | 0 |
| | | HeLa + MX | 3.577 | 29.280 | 4.936 | 0.705 |
| | B | HeLa | 3.266 | 4.915 | 3.805 | 0 |
| | | HeLa + MX | 2.627 | 24.323 | 4.346 | 0.824 |

Radioactivity counts are cpm of total or immunoprecipitated radioactivity per dish. Intervals: A - cells labeled overnight; B - parallel cultures after 24 hours' chase.

From the results shown in Table 2 it follows that p58X represents approximately 0.8% of the proteins in the cell extracts.

Very similar values were obtained in cultures after overnight incubation with labeled amino acids and in parallel cultures, which in addition were incubated for another 24 hours in "cold" media with a full complement of amino acids. Those results indicate that the values of radioactivity obtained reflect already an equilibrium state, rather than the velocity of incorporation; therefore, the values cannot be very different from the actual contents of p58X in the extracts. Extracts from cells labeled with [$^{35}$S]-methionine gave values of p58X similar to those of cells from extracts of cultures labeled with a mixture of [$^{14}$C]-amino acids.

Example 10

Immunoelectron and Scanning Microscopy of Control and of MX-infected HeLa Cells As indicated above in Example 1, MN antigen, detected by indirect immunofluorescence with MAb M75, is located on the surface membranes and in the nuclei of MX-infected HeLa cells or in HeLa cells grown in dense cultures. To elucidate more clearly the location of the MN antigen, immunoelectron microscopy was used wherein MAb M75 bound to MN antigen was visualized with immunogold beads. [Herzog et al., "Colloidal gold labeling for determining cell surface area," IN: Colloidal Gold, Vol. 3 (Hayat, M. A., ed.), pp. 139–149 (Academic Press Inc.; San Diego, Calif.)]

Ultrathin sections of control and of MX-infected HeLa cells are shown in FIGS. 13 A–D. Those immunoelectron micrographs demonstrate the location of MN antigen in the cells, and in addition, the striking ultrastructural differences between control and MX-infected HeLa. A control HeLa cell (FIG. 13A) is shown to have on its surface very little MN antigen, as visualised with gold beads. The cell surface is rather smooth, with only two little protrusions. No mitochondria can be seen in the cytoplasm. In contrast, MX-infected HeLa cells (FIGS. 13B and C) show the formation of abundant, dense filamentous protrusions from their surfaces. Most of the MN antigen is located on those filaments, which are decorated with immunogold. The cytoplasm of MX-infected HeLa contains numerous mitochondria (FIG. 13C). FIG. 13D demonstrates the location of MN antigen in the nucleus: some of the MN antigen is in nucleoplasm (possibly linked to chromatin), but a higher concentration of the MN antigen is in the nucleoli. Again, the surface of normal HeLa (panels A and E of FIG. 13) is rather smooth whereas MX-infected HeLa cells have on their surface, numerous filaments and "blebs". Some of the filaments appear to form bridges connecting them to adjacent cells.

It has been noted that in some instances of in vitro transformed cells compared to their normal parent cells that one of the differences is that the surface of normal cells was smooth whereas on the transformed cells were numerous hair-like protrusions [Darnell et al. "Molecular Cell Biology," (2nd edition) Sci. Am. Books; W. H. Freeman and Co., New York (1990)]. Under that criteria MX-infected HeLa cells, as seen in FIG. 13F, has a supertransformed appearance.

Further in some tumors, amplification of mitochondria has been described [Bernhard, W., "Handbook of Molecular Cytology," pp. 687–715, Lima de Faria (ed.), North Holland Publishing Co.; Amsterdam-London (1972)]. Such amplification was noted for MX-infected HeLa cells which stained very intensely with Janus' green, specific for mitochondria whereas control HeLa were only weakly stained.

It should be noted that electron microscopists were unable to find any structural characteristics specific for tumor cells.

Example 11

Antisense ODNs Inhibit MN Gene Expression

To determine whether both of the p54/58N proteins were encoded by one gene, the following experiments with antisense ODNs were performed. Previously sparse-growing HeLa cells were seeded to obtain an overcrowded culture and incubated for 130 hours either in the absence or in the presence of two gene-specific ODNs complementary to the 5' end of MN mRNA. HeLa cells were subcultured at 8×10⁵ cells per ml of DMEM with 10% FCS. Simultaneously, ODNs were added to the media as follows: (A) 29-mer ODN1 (5' CGCCCAGTGGGTCATCTTCCCCAGAAGAG 3', [SEQ. ID. NO.:3] complementary to positions 44–72) in 4 μM final concentration, (B) 19-mer ODN2 (5' GGAATC-CTCCTGCATCCGG 3', [SEQ. ID. NO.:4] complementary to positions 12–30) in 4 μM final concentration and (C) both ODN1 and ODN2 in 2 μM final concentration each. (D)

Cells treated in the same way, but incubated without ODNS, served as a control. After 130 hours, extracts from the cells were prepared and analyzed by immunoblotting using $^{125}$I-labeled MAb M75. Protein extracts from the cells were analyzed by immunoblotting and RIA using MAb M75. FIG. 3 provides the immunoblot results of those experiments.

It was found that cultivation of HeLa cells with the ODNs resulted in considerable inhibition of p54/58N synthesis. The 19-mer ODN2 (FIG. 3B) in 4 μM final concentration was very effective; as determined by RIA, it caused 40% inhibition, whereas the 29-mer ODN1 (4 μM) (FIG. 3A) and a combination of the two ODNs (FIG. 3C), each in 2 μM final concentration, were less effective in RIA showing a 25–35% increase of the MN-related proteins. At the same time, the amount of different HeLa cell protein determined by RIA using specific MAb H460 was in all cell variants approximately the same. Most importantly was that on immunoblot it could be seen that specific inhibition by the ODNs affected both of the p54/58N proteins. Thus, we concluded that the MN gene we cloned coded for both p54/58N proteins in HeLa cells.

Example 12

Northern Blotting of MN mRNA in Tumorigenic and Non-Tumorigenic Cell Lines

FIG. 4 shows the results of Northern blotting of MN mRNA in human cell lines. Total RNA was prepared from the following cell lines by the guanidinium thiocyanate-CsCl method: HeLa cells growing in a dense (A) and sparse (B) culture; CGL1 (H/F-N) hybrid cells (C); CGL3 (D) and CGL4 (E) segregants (both H/F-T); and human embryo fibroblasts (F). Fifteen μg of RNA were separated on a 1.2% formaldehyde gel and blotted onto a Hybond C Super membrane (Amersham). MN cDNA NotI probe was labeled by random priming (Multiprime DNA labelling system; Amersham). Hybridization was carried out in the presence of 50% formamide at 42° C., and the final wash was in 0.1% SSPE and 0.1% SDS at 65° C. An RNA ladder (0.24–9.5 kb) [Bethesda Research Laboratories (BRL); Bethesda, Md. (USA)] was used as a size standard.

Detected was a 1.5 kb MN-specific mRNA only in two tumorigenic segregant clones—CGL3 and CGL4 (H/F-T), but not in the non-tumorigenic hybrid clone CGL1 (H/F-N) or in normal human fibroblasts. Further, the 1.5 kb mRNA was found in the HeLa cells growing in dense (FIG. 4A) but not in sparse (FIG. 4B) culture.

Thus, the results of the Northern blotting were consistent with those of the above example in regard to MN-related proteins being associated with tumorigenicity.

Example 13

Southern Blotting of Genomic DNAs from Different Vertebrate Species to Detect MN Gene FIG. 5 illustrates the detection of MN genes in the genomic DNAs of various vertebrates by Southern blotting. Chromosomal DNA digested by SstI was as follows: (A) chicken; (B) bovine; (C) feline; (D) MX-infected HeLa cells; (E) mouse NIH 3T3 cells; (F) human placental cells; (G) HeLa cells; (H) sheep; (I) human melanoma cells; and (J) monkey Vero cells. Restriction fragments were separated on a 0.7% agarose gel and alkali blotted onto a Hybond N membrane (Amersham). The MN cDNA probe labelling and hybridization procedures were the same as for the Northern blotting analyses shown in FIG. 4 and described in Example 12.

The Southern blot of FIG. 5 made with SstI restriction fragments of chromosomal DNA shows in every species only one discrete band of about 1.5 kb. Further, such hybridizations with restriction fragments resulting from cleavage with XhoI and SalI gave in each chromosomal DNA sample only one band of 4.5 kb and 4.7 kb, respectively (data not shown). Those results indicate that the MN gene is present as a single copy in vertebrate genomes. The results further indicate that the MN gene together with its flanking sequences is rather conservative.

Since the cleavage sites of SstI create natural boundaries in the MN gene, and since the size of MN mRNA is the same as the size of the MN gene on Southern blot (compare FIGS. 4 and 5 and results of Example 12), it was inferred that there are no introns in the MN gene. That conclusion was also supported by the fact that restriction patterns of MN cDNA and of MN-specific genomic SstI fragments are the same.

The material listed below was deposited with the American Type Culture Collection (ATCC) in 10801 University Blvd., Manassas, Va. (USA). The deposits were made under the provisions of the Budapest Treaty on the International Recognition of Deposited Microorganisms for the Purposes of Patent Procedure and Regulations thereunder (Budapest Treaty). Maintenance of a viable culture is assured for thirty years from the date of deposit. The organism will be made available by the ATCC under the terms of the Budapest Treaty, and subject to an agreement between the Applicants and the ATCC which assures unrestricted availability upon issuance of the pertinent U.S. Patent. Availability of the deposited strain is not to be construed as a license to practice the invention in contravention of the rights granted under the authority of any Government in accordance with its patent laws.

| Hybridoma | Deposit Date | ATCC # |
| --- | --- | --- |
| VU-M75 | September 17, 1992 | HB 11128 |

The description of the foregoing embodiments of the invention have been presented for purposes of illustration and description. They are not intented to be exhaustive or to limit the invention to the precise form disclosed, and obviously many modifications and variations are possible in light of the above teachings. The embodiments were chosen and described in order to explain the principles of the invention and its practical application to enable thereby others skilled in the art to utilize the invention in various embodiments and with various modifications as are suited to the particular use contemplated. It is intended that the scope of the invention be defined by the claims appended hereto.

All references cited herein are hereby incorporated by reference.

What we claim is:

1. A method of imaging neoplastic disease in a patient, wherein said neoplastic disease is associated with abnormal expression of MN protein, comprising:
   (a) administering to said patient an MN-specific antibody or MN-specific antigen-binding fragment thereof which is linked to an imaging agent; and
   (b) detecting the binding of said antibody or antigen binding fragment thereof;
   wherein said MN-specific antibody or MN-specific antigen binding fragment thereof binds specifically to MN protein or MN polypeptide that is encoded by a nucleotide sequence selected from the group consisting of:
   (1) SEQ ID NO: 1's coding region;
   (2) nucleotide sequences that hybridize under stringent hybridization conditions of 50% formamide at 42° C. with a final wash of 0.1% SSPE and 0.1% SDS at 65° C. to complement of SEQ ID NO: 1's coding region; and
   (3) nucleotide sequences that differ from SEQ ID NO: 1's coding region or from the nucleotide sequences of (b) in codon sequence due to the degeneracy of the genetic code.

2. A method of detecting or detecting and quantifying MN protein and MN polypeptide, or MN protein, or MN polypeptide in a vertebrate sample comprising:
   (a) contacting said sample with an MN-specific antibody or an MN-specific antigen-binding fragment thereof; and
   (b) detecting or detecting and quantifying an amount of said antibody or antigen binding fragment thereof bound to MN protein and MN polypeptide, or MN protein, or MN polypeptide in said sample;
   wherein said MN-specific antibody or MN-specific antigen-binding fragment thereof binds specifically to MN protein or MN polypeptide that is encoded by a nucleotide sequence selected from the group consisting of:
   (1) SEQ ID NO: 1's coding region;
   (2) nucleotide sequences that hybridize under stringent hybridization conditions of 50% formamide at 42° C. with a final wash of 0.1% SSPE and 0.1% SDS at 65° C. to complement of SEQ ID NO: 1's coding region; and
   (3) nucleotide sequences that differ from SEQ. ID NO: 1's coding region or from the nucleotide sequences of (b) in codon sequence due to the degeneracy of the genetic code.

3. The method according to claim 2 wherein a competition immunoassay is employed to detect and quantify said MN protein or MN polypeptide, and wherein said method further comprises contacting said sample with labeled MN protein or labeled MN polypeptide which competes for binding to said antibody or antigen-binding fragment thereof with MN protein or MN polypeptide present in said sample.

4. The method according to claim 3 wherein the labeled MN protein or MN polypeptide is linked to a label selected from the group consisting of radionuclides, enzymes, coenzymes, fluorescers, chemiluminescers, chromogens, enzyme substrates or co-factors, enzyme inhibitors, free radicals, particles and dyes.

5. The method according to claim 2 which is diagnostic, or diagnostic and prognostic for neoplastic disease or for pre-neoplastic and neoplastic disease, wherein said disease is associated with abnormal expression of MN protein.

6. The method according to claim 5 wherein said pre-neoplastic or neoplastic disease is selected from the group consisting of pre-neoplastic or neoplastic diseases of the breast, bladder, ovary, vagina, vulva, uterus, uterine cervix, endometrium, prostate, kidney, lung, liver, skin, esophagus, colon, and head and neck, and squamous cell, adenosquamous, mesodermal, sarcoma, and melanoma tumors.

7. The method according to claim 2 wherein said detecting or detecting and quantifying is by immunohistochemical staining.

8. The method according to claim 2 wherein said detecting or detecting and quantifying method is selected from the group consisting of Western blots, enzyme-inked immunosorbent assays, radioimmunoassays, competition immunoassays, dual antibody sandwich assays, immunohistochemical staining assays, agglutination assays, and fluorescent immunoassays.

9. The method according to claim 2 wherein said antibody is an antigen binding antibody fragment.

10. The method according to claim 2 wherein said antibody is monoclonal.

11. The method according to claim 10 wherein said monoclonal antibody is secreted by the hybridoma VU-M75 which has Accession No. ATCC HB 11128.

12. The method according to claim 10 wherein said monoclonal antibody is prepared against an MN fusion protein.

13. The method according to claim 9 wherein said antigen binding antibody fragment is genetically engineered.

14. The method according to claim 2 wherein said MN protein has an amino acid sequence comprising more than 50 amino acids from SEQ ID NO: 2.

15. The method according to claim 2 wherein said sample is obtained from a mammal.

16. The method according to claim 2 wherein said sample is obtained from a human.

17. The method according to claim 2 wherein said sample is selected from the group consisting of tissue specimens, body fluids, tissue extracts and cell extracts.

18. The method according to claim 17 wherein said tissue specimens are from a uterine cervix.

19. The method according to claim 17 wherein the body fluids are selected from the group consisting of blood, serum, plasma, semen, breast exudate, saliva, tears, sputum, mucus, urine, lymph, cytosols, ascites, pleural effusions, amniotic fluid, bladder washes, bronchoalveolar lavages, and cerebrospinal fluid.

20. The method according to claim 2 wherein said antibody or antigen binding fragment thereof is labeled.

21. The method according to claim 20 wherein said antibody or antigen binding fragment thereof is linked to a label selected from the group consisting of radionuclides, enzymes, coenzymes, fluorescers, chemiluminescers, chromogens, enzyme substrates or co-factors, enzyme inhibitors, free radicals, particles and dyes.

22. The method according to claim 5 wherein said pre-neoplastic or neoplastic disease is selected from the group consisting of pre-neoplastic and neoplastic diseases of the breast, ovary, uterine cervix, endometrium, vagina, vulva, prostate, kidney, bladder, lung, liver, skin, esophagus, and colon and head and neck.

23. A method of detecting or detecting and quantifying in a vertebrate sample MN protein and MN polypeptide, or MN protein, or MN polypeptide, or detecting and quantifying in a vertebrate sample MN protein and MN polypeptide, or MN protein, or MN polypeptide comprising the steps of:

(a) incubating said sample with labeled MN protein or labeled MN polypeptide, and with an MN-specific antibody or an MN-specific antigen-binding fragment thereof;

(b) determining the amount of labeled MN protein or labeled MN polypeptide that is bound to said antibody or said antigen binding fragment thereof, and from that amount, determining the presence or absence of unlabeled MN protein and unlabeled MN polypeptide in said sample, or the amount of unlabeled MN protein in said sample, or the amount of unlabeled MN polypeptide in said sample, or so determining and, if present, quantifying the amount of unlabeled MN protein and unlabeled MN polypeptide in said sample, or the amount of unlabeled MN protein in said sample, or the amount of unlabeled MN polyeptide in said sample;

wherein said MN-specific antibody or MN-specific antigen-binding fragment thereof binds specifically to MN protein or MN polypeptide that is encoded by a nucleotide sequence selected from the group consisting of:

(1) SEQ ID NO: 1's coding region;

(2) nucleotide sequences that hybridize under stringent hybridization conditions of 50% formamide at 42° C. with a final wash of 0.1% SSPE and 0.1% SDS at 65° C. to complement of SEQ ID NO: 1's coding region; and (3) nucleotide sequences that differ from SEQ ID NO: 1's coding region or from the nucleotide sequences of (b) in codon sequence due to the degeneracy of the genetic code.

* * * * *

UNITED STATES PATENT AND TRADEMARK OFFICE
CERTIFICATE OF CORRECTION

PATENT NO. : 6,004,535
DATED : December 21, 1999
INVENTOR(S) : Jan Zavada et al.

It is certified that error appears in the above-identified patent and that said Letters Patent is hereby corrected as shown below:

Title Page,
Item [75] "Inventors: Jan Zavada; Silvia Pastorekova; Jaromir Pastorek, all of Bratislava, Czechoslovakia" should read --Jan Zavada, Prague, Czech Republic; Silvia Pastorekova; Jaromir Pastorek,both of Bratislava, Slovakia --;

Column 2,
Line 62, "58 kd. Upon non-reducing gels," should read -- 58 kd, upon non-reducing gels. --;

Column 5,
Line 13, "ELISAS" should read -- ELISAs --;
Line 53, "Beta" should read -- beta --;

Column 10,
Line 56, "(FIG.6)" should read --FIG. 6A-6B --;
Line 58, "FIGS. 6-9" should read -- FIGS. 6A-6B through 9 --;

Column 15,
Line 4, "eucaryote" should read -- eukaryote --;

Column 24,
Line 22, "diptheria" should read -- diphtheria --;

Column 25,
Lines 42-43, "Czechoslovakia" should read -- Slovak Republic --;
Line 44, "sera" should read -- serum --;

Column 28,
Line 46 and 64, "(FIG.6)" should read --FIG. 6A-6B --;

Column 29,
Line 7, "radimmunoassay" should read -- radioimmunoassay --;
Line 14 and 15,"(FIG.6)" should read -- FIG. 6A-6B --;
Line 19, "(top graph of FIG.6)" should read -- (FIG. 6A) --;
Line 21, "(bottom graph of FIG.6)" should read -- (FIG. 6B) --;

UNITED STATES PATENT AND TRADEMARK OFFICE
CERTIFICATE OF CORRECTION

PATENT NO. : 6,004,535
DATED : December 21, 1999
INVENTOR(S) : Jan Zavada et al.

It is certified that error appears in the above-identified patent and that said Letters Patent is hereby corrected as shown below:

Column 31,
Line 57, "FIG. 11" should read -- FIG. 11A-11B --;

Column 33,
Line 54, "FIG. 13 A-D" should read -- FIG. 13A-13D --; and

Column 35,
Line 14, "increase" should read -- decrease --.

Signed and Sealed this

Nineteenth Day of June, 2001

*Attest:*

*Attesting Officer*

NICHOLAS P. GODICI
*Acting Director of the United States Patent and Trademark Office*

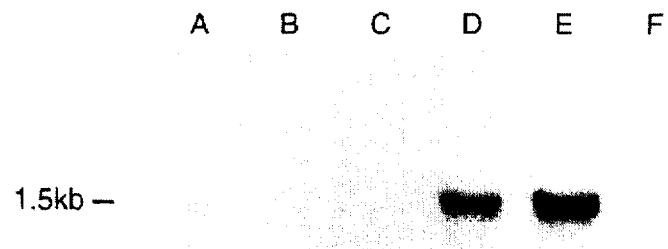
FIG._4
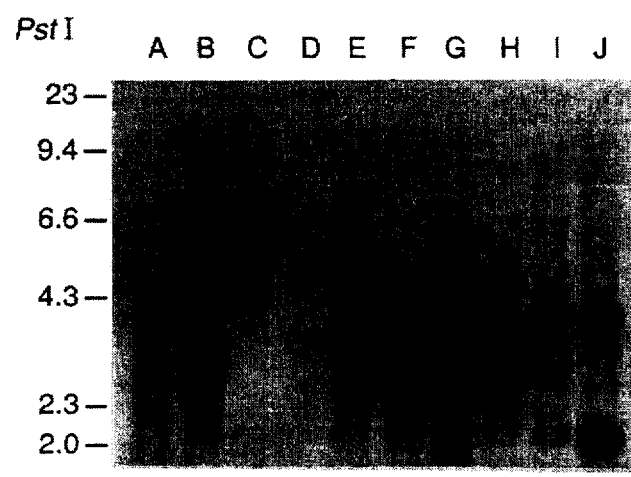
FIG._5

UNITED STATES PATENT AND TRADEMARK OFFICE
CERTIFICATE OF CORRECTION

PATENT NO. : 6,004,535
DATED : December 21, 1999
INVENTOR(S) : Jan Zavada et al.

Page 1 of 1

It is certified that error appears in the above-identified patent and that said Letters Patent is hereby corrected as shown below:

Column 2,
Line 63, "58 kd, upon non-reducing gels." should read -- 58 kd. Upon non-reducing gels, --;

Column 22,
Line 7, "Czechoslovakia" should read -- Slovak Republic --;

Column 44,
Line 63, "or detecting and quantifying" should be deleted.

Signed and Sealed this

Twelfth Day of March, 2002

Attest:

Attesting Officer

JAMES E. ROGAN
Director of the United States Patent and Trademark Office